United States Patent
Sawayama et al.

(10) Patent No.: US 10,085,928 B2
(45) Date of Patent: Oct. 2, 2018

(54) DIGLYCERIN DERIVATE-MODIFIED SILICONE, EMULSIFIER FOR WATER-IN-OIL EMULSION USING THE SAME, EXTERNAL USE PREPARATON, AND COSMETIC COMPOSITION

(71) Applicant: Dow Corning Toray Co., Ltd., Tokyo (JP)

(72) Inventors: Sayuri Sawayama, Ichihara (JP); Seiki Tamura, Ichihara (JP); Seiji Hori, Ichihara (JP)

(73) Assignee: DOW CORNING TORAY CO., LTD., Tokyo (JP)

(*) Notice: Subject to any disclaimer, the term of this patent is extended or adjusted under 35 U.S.C. 154(b) by 111 days.

(21) Appl. No.: 14/369,253

(22) PCT Filed: Dec. 26, 2012

(86) PCT No.: PCT/JP2012/084285
§ 371 (c)(1),
(2) Date: Jun. 27, 2014

(87) PCT Pub. No.: WO2013/103147
PCT Pub. Date: Jul. 11, 2013

(65) Prior Publication Data
US 2015/0004107 A1 Jan. 1, 2015

(30) Foreign Application Priority Data
Dec. 27, 2011 (JP) .................. 2011-286977

(51) Int. Cl.
| | | |
|---|---|---|
| *A61K 8/58* | (2006.01) | |
| *A61K 8/892* | (2006.01) | |
| *A61K 8/06* | (2006.01) | |
| *C08J 3/03* | (2006.01) | |
| *C08G 77/14* | (2006.01) | |
| *C08G 77/24* | (2006.01) | |
| *C08G 77/38* | (2006.01) | |
| *C08L 83/06* | (2006.01) | |
| *B01F 17/54* | (2006.01) | |
| *A61Q 15/00* | (2006.01) | |
| *A61Q 19/00* | (2006.01) | |
| *A61Q 1/00* | (2006.01) | |
| *A61Q 1/02* | (2006.01) | |
| *A61Q 1/06* | (2006.01) | |
| *A61Q 1/10* | (2006.01) | |
| *A61Q 17/04* | (2006.01) | |

(Continued)

(52) U.S. Cl.
CPC ............. *A61K 8/585* (2013.01); *A61K 8/064* (2013.01); *A61K 8/892* (2013.01); *A61Q 1/00* (2013.01); *A61Q 1/02* (2013.01); *A61Q 1/06* (2013.01); *A61Q 1/10* (2013.01); *A61Q 15/00* (2013.01); *A61Q 17/04* (2013.01); *A61Q 19/00* (2013.01); *A61Q 19/002* (2013.01); *A61Q 19/02* (2013.01); *A61Q 19/04* (2013.01); *B01F 17/0071* (2013.01); *C07F 7/0852* (2013.01); *C08G 77/14* (2013.01); *C08G 77/24* (2013.01); *C08G 77/38* (2013.01); *C08J 3/03* (2013.01); *C08L 83/06* (2013.01); *A61K 2800/10* (2013.01); *A61K 2800/30* (2013.01); *A61Q 5/02* (2013.01); *A61Q 19/10* (2013.01)

(58) Field of Classification Search
CPC ........ A61K 8/892; A61K 8/585; A61K 8/064; A61K 2800/10; A61K 2800/30; C08J 3/03; C08G 77/14; C08G 77/24; C08G 77/38; C08L 83/06; A61Q 17/04; A61Q 1/10; A61Q 1/06; A61Q 1/02; A61Q 1/00; A61Q 19/04; A61Q 19/02; A61Q 19/002; A61Q 15/00; A61Q 19/00; A61Q 5/02; A61Q 19/10; C07F 7/0852; B01F 17/0071
See application file for complete search history.

(56) References Cited

U.S. PATENT DOCUMENTS

| | | | |
|---|---|---|---|
| 4,122,029 | A | 10/1978 | Gee et al. |
| 4,268,499 | A | 5/1981 | Keil |

(Continued)

FOREIGN PATENT DOCUMENTS

| | | |
|---|---|---|
| EP | 0 176 884 A2 | 4/1986 |
| EP | 0 612 759 A1 | 8/1994 |

(Continued)

OTHER PUBLICATIONS aciscience.org—"Chemical Properties and Derivatives of Glycerol." Retrieved on May 20, 2016. Retrieved from the internet <URL: http://www.aciscience.org/docs/chemical_properties_and_derivatives_of_glycerol.pdf>.*

(Continued)

*Primary Examiner* — Doan T Phan
(74) *Attorney, Agent, or Firm* — Howard & Howard Attorneys PLLC

(57) ABSTRACT

A diglycerin derivative-modified silicone, wherein the diglycerin derivative-modified silicone contains a long chain alkyl group as a lipophilic group in a molecule, does not have an oxyalkylene structure wherein an average value of the number of repetitions of the oxyalkylene unit is two or more, has only a glycerin derivative group with an average value of the number of repetitions of glycerin units of 1.1 to 2.9 as a hydrophilic group, and does not have other hydrophilic group in the molecule; a surfactant and dispersing agent, an emulsifier for a water-in-oil emulsion, an external use preparation, and a cosmetic composition containing the same.

15 Claims, No Drawings

(51) Int. Cl.
*A61Q 19/02* (2006.01)
*A61Q 19/04* (2006.01)
*C07F 7/08* (2006.01)
*A61Q 5/02* (2006.01)
*A61Q 19/10* (2006.01)

(56) References Cited

U.S. PATENT DOCUMENTS

| | | | |
|---|---|---|---|
| 4,381,241 | A | 4/1983 | Romenesko et al. |
| 4,431,789 | A | 2/1984 | Okazaki et al. |
| 4,689,383 | A | 8/1987 | Riffle et al. |
| 4,698,178 | A | 10/1987 | Huttinger et al. |
| 4,853,474 | A | 8/1989 | Bahr et al. |
| 4,908,228 | A | 3/1990 | Lo |
| 4,963,093 | A | 10/1990 | Dragan |
| 5,831,080 | A | 11/1998 | Sejpka et al. |
| 6,218,560 | B1 | 4/2001 | Abele et al. |
| 6,784,271 | B2 | 8/2004 | Nakanishi |
| 7,771,709 | B2 | 8/2010 | Nakanishi et al. |
| 8,288,498 | B2 | 10/2012 | Hayashi et al. |
| 8,784,787 | B2 | 7/2014 | Tamura et al. |
| 2002/0131947 | A1* | 9/2002 | Nakanishi ............ A61K 8/0212 424/70.12 |
| 2009/0062459 | A1 | 3/2009 | Thum et al. |
| 2009/0203802 | A1 | 8/2009 | Kamei et al. |
| 2010/0266651 | A1 | 10/2010 | Czech et al. |
| 2012/0269747 | A1 | 10/2012 | Iimura et al. |
| 2014/0004065 | A1 | 1/2014 | Souda et al. |

FOREIGN PATENT DOCUMENTS

| | | | |
|---|---|---|---|
| EP | 1 004 614 | A1 | 5/2000 |
| JP | S 57-149290 | A | 9/1982 |
| JP | S 62-068820 | A | 3/1987 |
| JP | S 63-139106 | A | 6/1988 |
| JP | H 02-228958 | A | 9/1990 |
| JP | H 05-186596 | A | 7/1993 |
| JP | H 06-145023 | A | 5/1994 |
| JP | H 06-089147 | B2 | 11/1994 |
| JP | H 08-269204 | A | 10/1996 |
| JP | 2583412 | B | 2/1997 |
| JP | 2613124 | B | 5/1997 |
| JP | 10-310509 | * | 11/1998 |
| JP | H 10-310509 | A | 11/1998 |
| JP | H 10-316526 | A | 12/1998 |
| JP | H 10-316527 | A | 12/1998 |
| JP | H 10-316536 | A | 12/1998 |
| JP | H 10-316540 | A | 12/1998 |
| JP | 2844453 | B | 1/1999 |
| JP | 2002-179798 | A | 6/2002 |
| JP | 3389311 | B | 3/2003 |
| JP | 3513682 | B | 3/2004 |
| JP | 2004-169015 | A | 6/2004 |
| JP | 2004-231605 | A | 8/2004 |
| JP | 2004-231607 | A | 8/2004 |
| JP | 2004-231608 | A | 8/2004 |
| JP | 2005-042097 | A | 2/2005 |
| JP | 2005-089494 | A | 4/2005 |
| JP | 3678420 | B | 8/2005 |
| JP | 2005-232088 | A | 9/2005 |
| JP | 2005-344076 | A | 12/2005 |
| JP | 2006-218472 | A | 8/2006 |
| JP | 2008-274241 | A | 11/2008 |
| JP | 4187198 | B2 | 11/2008 |
| JP | 4485134 | B2 | 6/2010 |
| WO | WO 2006/127883 | A2 | 11/2006 |
| WO | WO 2007/109240 | A2 | 9/2007 |
| WO | WO 2008/046763 | A1 | 4/2008 |
| WO | WO 2009/006091 | A2 | 1/2009 |
| WO | WO 2011/028765 | A1 | 3/2011 |
| WO | WO 2011/028770 | A1 | 3/2011 |
| WO | WO 2011/136397 | A1 | 3/2011 |
| WO | WO 2011/049246 | A1 | 4/2011 |
| WO | WO 2011/049248 | A1 | 4/2011 |
| WO | WO 2013/100169 | A1 | 7/2013 |

OTHER PUBLICATIONS

International Search Report for Application No. PCT/JP2012/084269 dated Apr. 29, 2013, 3 pages.
International Search Report for Application No. PCT/JP2012/084285 dated Apr. 24, 2013, 3 pages.
Machine-assisted English language abstract for EP 0 176 884 extracted from espacenet.com database on Aug. 28, 2014, 1 pages.
English language abstract for EP 0 612 759 extracted from espacenet.com database on Aug. 28, 2014, 1 pages.
English language abstract for EP 1 004 614 extracted from espacenet.com database on Aug. 28, 2014, 2 pages.
English language abstract for JPS 57-149290 extracted from espacenet.com database on Aug. 28, 2014, 2 pages.
English language abstract for JPS 62-068820 extracted from PAJ database on Aug. 28, 2014, 1 page.
English language abstract for JPS 63-139106 extracted from PAJ database on Aug. 28, 2014, 1 page.
English language abstract for JPH 02-228958 extracted from espacenet.com database on Aug. 28, 2014, 2 pages.
English language abstract and machine-assisted English translation for JPH 05-186596 extracted from the PAJ database on Aug. 28, 2014, 33 pages.
English language abstract and machine-assisted English translation for JPH 06-145023 extracted from the PAJ database on Aug. 28, 2014, 22 pages.
English language abstract for JPH 06-089147 extracted from espacenet.com database on Aug. 27, 2014, 2 pages.
English language abstract and machine-assisted English translation for JPH 08-269204 extracted from the PAJ database on Aug. 28, 2014, 29 pages.
Machine-assisted English translation for JP 2583412 extracted from the PAJ database on Aug. 28, 2014, 15 pages.
Machine-assisted English translation for JP 2613124 extracted from the PAJ database on Aug. 28, 2014, 43 pages.
English language abstract and machine-assisted English translation for JPH 10-310509 extracted from the PAJ database on Sep. 3, 2014, 22 pages.
English language abstract and machine-assisted English translation for JPH 10-316526 extracted from the PAJ database on Aug. 28, 2014, 19 pages.
English language abstract and machine-assisted English translation for JPH 10-316527 extracted from the PAJ database on Aug. 28, 2014, 20 pages.
English language abstract and machine-assisted English translation for JPH 10-316536 extracted from the PAJ database on Aug. 28, 2014, 21 pages.
English language abstract and machine-assisted English translation for JPH 10-316540 extracted from the PAJ database on Aug. 28, 2014, 21 pages.
Machine-assisted English translation for JP 2844453 extracted from the PAJ database on Aug. 27, 2014, 36 pages.
English language abstract for JP 2002-179798 extracted from espacenet.com database on Aug. 28, 2014, 2 pages.
Machine-assisted English translation for JP 3389311 extracted from the PAJ database on Aug. 27, 2014, 42 pages.
Machine-assisted English translation for JP 3513682 extracted from the PAJ database on Aug. 28, 2014, 20 pages.
English language abstract for JP 2004-169015 extracted from espacenet.com database on Aug. 28, 2014, 2 pages.
English language abstract and machine-assisted English translation for JP 2004-231605 extracted from the PAJ database on Aug. 28, 2014, 43 pages.
English language abstract and machine-assisted English translation for JP 2004-231607 extracted from the PAJ database on Aug. 28, 2014, 44 pages.
English language abstract and machine-assisted English translation for JP 2004-231608 extracted from the PAJ database on Aug. 28, 2014, 50 pages.
English language abstract for JP 2005-042097 extracted from espacenet.com database on Aug. 27, 2014, 2 pages.

(56) References Cited

OTHER PUBLICATIONS

English language abstract and machine-assisted English translation for JP 2005-089494 extracted from the PAJ database on Aug. 27, 2014, 30 pages.

Machine-assisted English translation for JP 3678420 extracted from the PAJ database on Aug. 28, 2014, 63 pages.

English language abstract and machine-assisted English translation for JP 2005-232088 extracted from the PAJ database on Sep. 3, 2014, 22 pages.

English language abstract and machine-assisted English translation for JP 2005-344076 extracted from the PAJ database on Aug. 27, 2014, 23 pages.

English language abstract and machine-assisted English translation for JP 2006-218472 extracted from the PAJ database on Aug. 27, 2014, 27 pages.

English language abstract for JP 2008-274241 extracted from espacenet.com database on Aug. 28, 2014, 2 pages.

English language abstract not found for JP 4187198; however, see English language equivalent U.S. Pat. No. 6,784,271. Original document extracted from esapcenet.com database on Aug. 28, 2014, 32 pages.

English language abstract and machine-assisted English translation for JP 4485134 extracted from the PAJ database on Aug. 27, 2014, 92 pages.

English language abstract for WO 2011/049246 extracted from espacenet.com database on Aug. 28, 2014, 2 pages.

English language abstract for WO 2011/049248 extracted from espacenet.com database on Aug. 28, 2014, 2 pages.

Kumano et al., "Studies of Water-In-Oil (w/o) Emulsion Stabilized with Amino Acids or Their Salts," J. Soc. Cosmet. Chem., 28, pp. 285-314 (May 1977).

Yamaguchi, "Progress on W/O Emulsification Technique", J. Soc. Cosmet. Chem., 26, pp. 229-237(1993).

\* cited by examiner

US 10,085,928 B2

DIGLYCERIN DERIVATE-MODIFIED SILICONE, EMULSIFIER FOR WATER-IN-OIL EMULSION USING THE SAME, EXTERNAL USE PREPARATON, AND COSMETIC COMPOSITION

CROSS-REFERENCE TO RELATED APPLICATIONS

This application is the National Stage of International Patent Application No. PCT/JP2012/084285, filed on Dec. 26, 2012, which claims priority to and all the advantages of Japanese Patent Application No. 2011-286977, filed on Dec. 27, 2011, the content of which is incorporated herein by reference.

TECHNICAL FIELD

The present invention relates to a diglycerin derivative-modified silicone that has a long chain monovalent hydrocarbon group having 9 to 30 carbons per molecule, that does not have an oxyalkylene structure wherein an average value of the number of repetitions of the oxyalkylene unit is two or more, and that is modified by a diglycerin derivative group as a hydrophilic group; a composition containing the same; a surfactant and dispersing agent containing these; and particularly relates to an emulsifier for a water-in-oil emulsion. In addition, the present invention relates to the diglycerin derivative-modified silicone, a composition containing the same, a water-in-oil emulsion containing these, and an external use preparation and a cosmetic composition containing these. Furthermore, the present invention relates to a diglycerin derivative-modified silicone able to be designed as a completely polyoxyethylene (PEG)-FREE formulation without impairing the effect of improved feel brought about by a diglycerin derivative-modified silicone due to particularly excellent emulsification and dispersion stabilities in an oil phase when used alone, and a surfactant and dispersing agent, emulsifier for a water-in-oil emulsion, external use preparation or cosmetic composition containing the same.

BACKGROUND ART

Silicones having hydrophilic groups exhibit excellent surface activity due to possessing both a silicone moiety, which exhibits properties such as hydrophobicity, softness, lubricity and chemical stability, and a hydrophilic group moiety, which exhibits properties such as hydrophilicity, moisture retention properties and adhesive properties. Therefore, silicones having hydrophilic groups are widely used in foods, resins, coatings, cosmetic compositions and the like, and a variety of hydrophilic silicone compounds have been known in the past. In particular, silicone oils such as low molecular weight cyclic siloxanes are often blended in order to improve the sensation during use of a cosmetic composition, and polyether-modified silicones (polyether-modified polysiloxanes) are widely used as cosmetic composition raw materials such as surfactants due to exhibiting good compatibility with silicone oils.

In the field of cosmetic products, emulsifiers for water-in-oil emulsions is the use in which the value of polyether-modified silicones is maximized. Water-in-oil emulsion systems exhibit better moisture resistance than oil-in-water emulsions and have the characteristic of being able to maintain an effect such as cosmetic retainability. However, stabilizing water-in-oil emulsions has historically been more difficult than stabilizing oil-in-water emulsions, and until about 30 years ago, the only method for stabilizing water-in-oil emulsions was by solidifying an oil phase (external phase) with a wax (a beeswax-Borax-based emulsifier), which led to poor usability and sensation during use as a cosmetic product. In addition, this technique involved problems such as difficulty in maintaining stability in regions having wide temperature variations and difficulty in adjusting the feeling to touch by altering the oil phase/aqueous phase ratio.

After this, an amino acid gel emulsification method (Non-Patent Document 1) and a high internal phase W/O emulsion using this method were developed in 1977, and a breakthrough was achieved by ameliorating the oily sensation during use by being able to reduce the quantity of the oil phase and gelling the oil phase by means of a lamellar structure obtained by arranging an amino acid and a surfactant in a regular manner, thereby improving the stability of the emulsion. Furthermore, a method for obtaining a stable W/O emulsion by adding an aqueous phase to an oily gel obtained by using a clay mineral that was hydrophobized/oil-swelled by means of a quaternary ammonium salt-based organic cation and the like (Non-Patent Document 2) was developed, and this contributed to broadening the scope of formulations according to the texture and feeling to touch of a water-in-oil emulsion cosmetic composition. However, these conventional W/O emulsion stabilization techniques were developed in order to maintain the stability of a system by gelling or solidifying an oil phase (external phase), meaning that it was difficult to stabilize an emulsion while maintaining a low emulsion viscosity.

With a technique for producing a W/O emulsion having excellent stability while having a low viscosity and good fluidity, it would be possible to obtain a practical W/O emulsion cosmetic composition having a soft feeling to touch, light smoothness and good spreadability. That is, by using this technique in a combination with conventional formulation techniques for obtaining a stable cream, it is possible to freely adjust the texture or feeling to touch of a cosmetic composition according to consumers' wishes and the intended use of the cosmetic composition, and such a composition was thought to be of high value. Therefore, attempts were made to improve the feeling to touch by using the aforementioned techniques in a formulation obtained by adding a silicone oil to an oil phase. However, it is not possible to stably gel a silicone oil by using the aforementioned techniques, and it was not possible to obtain a W/O emulsion cosmetic composition having excellent stability and feeling to touch.

Under such circumstances, attention was focused purely on emulsification performance, not hardening oils, and research into the use of polyether-modified silicones in emulsifiers for water-in-oil emulsions was carried out, mainly in the USA and Europe (Patent Documents 1 to 5). Until around 1985, polyether-modified dimethylpolysiloxanes functioned as useful emulsifiers for oil phases that primarily contain silicone oils, long chain alkyl/polyether-comodified dimethylpolysiloxanes functioned as useful emulsifiers for oil phases that primarily contain organic oils or mixed oils of silicone oils and organic oils, and these were confirmed as having the previously unachievable property of obtaining a W/O emulsion cosmetic composition having both more excellent stability and lower viscosity than previous compositions. <

Thereafter, organic emulsifiers that produced water-in-oil emulsions having low viscosity and excellent stability, such as polyglyceryl polyhydroxystearates and isostearyl glyceryl, were developed, but these materials do not have a silicone moiety in the structure, and therefore have the problem of being unable to obtain a stable emulsion in formulations in which the proportion of a silicone oil in an oil phase is high. In addition, these materials are inferior to polyether-modified silicones in terms of feeling to touch. Therefore, these emulsifiers for organic W/O emulsions are often used in combination with polyether-modified silicones in, for example, formulations in which the proportion of a silicone oil in an oil phase is high.

This is one reason why polyether-modified silicones currently occupy an important position in the field of emulsifiers for water-in-oil emulsions used in cosmetic products.

Meanwhile, glycerin-modified silicones have long been known as non-ionic hydrophilic silicones that differ from polyether-modified silicones (Patent Documents 6 to 19), and investigations into the use of these in cosmetic compositions have increased. However, stable production of glycerin-modified silicones is extremely difficult technically, and unsaturated group-containing glycerin derivatives, which are raw materials of glycerin-modified silicones, are expensive and are difficult to procure on an industrial scale. As a result, the number of commercially available glycerin-modified silicone products is far lower than that of polyether-modified silicones, and because these are also expensive, actual use of glycerin-modified silicones has been limited.

Recently, it has been thought that glycerin-modified silicone was superior to polyether-modified silicone from the perspective of oxidation stability and, thus, glycerin-modified silicone has attracted attention as a surfactant having greater safety. For example, in Germany, a demand for the replacement of raw materials having polyether groups with non-polyether raw materials has increased due to a negative perception of the safety of products comprising polyoxyethylene (PEG) due to testing done by a consumer information magazine company. Moreover, in South Korea, increased interest in non-polyether silicone surfactants has emerged due to a concern that products containing polyoxyethylene (PEG) may irritate the skin because formalin may be produced as a result of oxidation degradation of PEG.

In light of the above, there is a global trend toward changing the entire formulation of end consumer products such as cosmetic products, and the like, to PEG-FREE formulations. In concord with this trend, there is a demand for progression from the old polyether-modified silicone technology to non-polyether hydrophilic silicone in the field of silicone-based surfactants as well. However, as well as being expensive, conventional glycerin-modified silicones have significant problems in that they do not appear in patent document searches. This is because even if glycerin-modified silicone is used as an emulsifier for a water-in-oil emulsion, it cannot be used in an actual formulation because performance is low. As a result, there is no choice but to use a more reliable polyether-modified silicone emulsifier in combination with the glycerin-modified silicone, which makes it impossible to achieve the goal of shifting all cosmetic compositions to PEG-FREE formulations.

More specifically, an undecyl glyceryl ether-modified organopolysiloxane that is disclosed in Patent Document 11 can form a stable W/O emulsion if the oil phase is a silicone oil, but cannot form a stable emulsion in formulations in which an oil phase is a mixed system of an organic oil and a silicone oil or an oil phase primarily contains an organic oil. Therefore, an undecyl glyceryl ether-modified organopolysiloxane cannot be used alone as an emulsifier in this type of formulation, and it is essential for the formulation to be aided by an organic emulsifier or a long chain alkyl/polyether-comodified dimethylpolysiloxane.

In addition, the polyhydric alcohol-modified silicone disclosed in Patent Document 14 is characterized by having a linear siloxane branch as a lipophilic group in the structure, and types having a triglycerin group as a hydrophilic group and a medium chain alkyl group as an optional secondary lipophilic group are commercially available. By having two lipophilic groups in the structure, this material can be used in a wider range of oil agents than the material disclosed in Patent Document 11. Specifically, it is possible to form a stable W/O emulsion with a silicone oil, an ester oil in which the alkyl chain length is not long, a triglyceride, or a mixed oil comprising a silicone oil and a variety of organic oils. However, in cases where the oil phase comprises a non-polar organic oil such as a mineral oil and isododecane or in the case of a mixed oil system in which the proportion of these non-polar oils is high, it is not possible to reduce the emulsion particle diameter due to emulsification performance being poor, particles agglomerate over time or when subjected to heat, and the emulsion separates. As a result, this polyhydric alcohol-modified silicone cannot be used alone as an emulsifier in this type of formulation, and it is essential for the formulation to be aided by an oil-gelling agent such as an organic emulsifier, a long chain alkyl/polyether-comodified dimethylpolysiloxane and a clay mineral that has been hydrophobized/oil-swelled by means of a quaternary ammonium salt-based organic cation and the like.

The branched polyglycerol-modified silicone disclosed in Patent Document 15 is produced by addition/graft polymerizing 2,3-epoxy-1-propanol with a silicone having one or more functional group selected from among the group comprising a hydroxy group, a carboxy group, an amino group, an imino group, a mercapto group and an epoxy group in the presence of an acidic or basic catalyst. However, with this method, the siloxane backbone disconnects during the graft polymerization, which results in two or more components having different properties being prone to be produced as the copolymer. This leads to a multitude of problems related to variable product quality, refining processes, and the like. Therefore, this is an extremely important material for maintaining the stability and emulsion viscosity of an oil-water mixture, that is, a material that is not suited to the functions of an emulsifier. In addition, because branched polyglycerol groups contain an extremely high number of hydroxyl groups per hydrophilic group, when modifying a silicone with the hydrophilic group, the hydrophilic/lipophilic balance (HLB) readily breaks down due to small variations in the degree of modification caused by reaction conditions or raw material considerations, meaning that the stability, viscosity or the like of the W/O emulsion varies greatly according to the branched polyglycerol-modified silicone lot. Therefore, branched polyglycerol groups exhibit an excessively strong autoagglutination force, and therefore tend to significantly increase the viscosity of a branched polyglycerol-modified silicone, meaning that compatibility between an oil phase and a modified silicone is reduced, energy transfer efficiency during mechanical emulsification is reduced, and it is extremely difficult to obtain a stable W/O emulsion having a fine particle diameter.

When explained in relation to the field of cosmetic products, the both terminal silicone-modified glycerin disclosed in Patent Documents 18 and 19 is a material that achieves excellent performance as an agent for dispersing a powder in an oil in cases where the oil phase is a silicone oil, and is a material in which the function as an emulsifier for a water-in-oil emulsion is low both inherently and in terms of being usable with a wide variety of oil agents.

Among Patent Documents 6 to 19, which relate to glycerin-modified silicones, the four technologies mentioned above are used in currently commercially available products. Therefore, it is thought that materials other than these have been judged by the applicant to exhibit insufficient value or effect to be commercialized.

With this in mind, the inventors of the present invention realized the following matters. Applications of monoglycerin-modified silicones, triglycerin-modified silicones and polyglycerin-modified silicones having many glycerin units in cosmetic compositions have been reported in many patent documents, and performance limits of these silicones as emulsifiers for water-in-oil emulsions are clear from market research. However, there has been very little research that focuses on diglycerin-modified silicones (Patent Document 13), and of the many past patent documents that relate to the use of glycerin-modified silicones other than this in cosmetic compositions, only 12 documents disclose diglycerin-modified silicones in practical examples (Patent Document 14 and Patent Documents 20 to 30). Furthermore, only Patent Documents 13 and 26 investigate diglycerin-modified silicones as emulsifiers for water-in-oil emulsions.

More specifically, in Patent Document 14, the siloxane compound 1 in the practical examples corresponds to a diglycerin-modified silicone, but only the detergent composition in Practical Example 1, the make-up remover in Practical Example 8 and the make-up remover in Practical Example 11 relate to the blending of this siloxane compound 1 in a cosmetic composition, and all three are aqueous systems that do not contain an oil component. Therefore, these documents do not investigate the use of diglycerin-modified silicones as emulsifiers for water-in-oil emulsions.

Patent Documents 20 to 24, 28 and 29 are formulations that are completely different from water-in-oil emulsions, and therefore do not mention investigations into the use of diglycerin-modified silicones in this type of use. Patent Document 25 relates to a method for refining a modified silicone compound having a branched polymer comprising a hydrophilic group, and only discloses a method for producing a deodorized diglycerin-modified silicone in Practical Example 5 and preparing a non-aqueous oil-based foundation using this deodorized diglycerin-modified silicone in Practical Example 14. Therefore, these documents do not investigate the use of diglycerin-modified silicones as emulsifiers for water-in-oil emulsions. In addition, Patent Document 30 discloses a technique for providing a cosmetic composition containing a silicone oil-containing oil agent and having excellent emulsion stability, but only discloses a diglycerin-modified silicone in Synthesis Example 5, and does not disclose a practical example in which this diglycerin-modified silicone is actually blended in a cosmetic composition.

Patent Document 26 relates to a cosmetic composition that is characterized by containing a clay mineral and the polyhydric alcohol-modified silicone disclosed in Patent Document 14, and Production Example 6 discloses a diglycerin-modified silicone having a specific structure. In addition, Practical Example 14 discloses a water-in-oil cream that contains this diglycerin-modified, silicone and dimethyldistearyl ammonium hectorite. However, because the viscosity of the emulsion is too low when the diglycerin-modified silicone of Production Example 6 is used as an emulsifier, stability cannot be maintained unless the oil phase is thickened by means of the clay mineral. In addition, this diglycerin-modified silicone has poor compatibility with a variety of organic oils, and even if the clay mineral is additionally used in a formulation in which the proportion of an organic oil in the oil phase is high, the stability of the emulsion cannot be maintained.

Patent Document 27 is an invention that relates to a powder composition and powder-in-oil dispersion comprising a powder and/or a coloring agent and, of the polyhydric alcohol-modified silicones disclosed in Patent Document 14, a polyglycerin-modified silicone having a linear siloxane branch, and also relates to a cosmetic composition containing these, and Production Example 1 discloses a diglycerin-modified silicone having a specific structure. Practical Example 1 discloses a powder-in-oil dispersion, Practical Example 5 discloses a powder composition, Practical Examples 9 and 13 disclose sunscreen agents, Practical Example 17 discloses an oil-in-water cream, Practical Example 21 discloses a water-in-oil cream, Practical Example 23 discloses a foundation, Practical Example 29 discloses an eye liner, Practical Examples 37 and 38 disclose a sun-screening milky lotion, Practical Example 40 discloses an O/W sun-screening milky lotion, and these contain this diglycerin-modified silicone. However, in all of these water-in-oil emulsion-based formulations (Practical Examples 9, 13, 21, 23, 29, 37 and 38), the diglycerin-modified silicone is used as a powder dispersing agent or an agent for treating the surface of a powder, and a polyether-modified silicone and/or a crosslinked polyether-modified silicone is used as an emulsifier for a water-in-oil emulsion in all of these examples. Therefore, these documents do not investigate the use of diglycerin-modified silicones as emulsifiers for water-in-oil emulsions. Furthermore, this diglycerin-modified silicone has poor compatibility with a variety of organic oils, and it is not possible to obtain a stable powder-in-oil dispersion in a formulation in which the proportion of an organic oil in the oil phase is high.

Patent Document 13 discloses a glyceryl ether-modified organo(poly)siloxane having a specific structure, a method for producing same, and a cosmetic composition containing the same, and Practical Examples 2, 4, 6 and 8 disclose compounds corresponding to diglycerin-modified silicones and methods for producing same. In addition, the results of an emulsification test (water-in-oil emulsion) of a simple formulation comprising the compound of Practical Example 2, a silicone oil and water are reported in Experimental Example 1, and the results obtained by blending the compound of Practical Example 2 in a hair rinse (aqueous system) having a specific composition are reported in Cosmetic Composition Formulation Example 1. However, the diglycerin-modified silicones disclosed in Practical Examples 2, 4, 6 and 8 exhibit poor compatibility with a variety of organic oils, and it is not possible to obtain a stable W/O emulsion in a formulation in which the proportion of an organic oil in the oil phase is high, meaning that separation occurs over time or when subjected to heat. Therefore, an undecyl glyceryl ether-modified organopolysiloxane cannot be used alone as an emulsifier in this type of formulation, and it is essential for the formulation to be aided by an organic emulsifier or a long chain alkyl/polyether-comodified dimethylpolysiloxane.

In Patent Document 31, the applicant of the present application proposes the use of a co-modified organopolysiloxane copolymer having a group that has a carbosiloxane dendron structure and a hydrophilic group such as glycerin and a polyhydric alcohol in the molecule as a surfactant, powder treatment agent or surface treatment agent able to be advantageously used in the field of cosmetic compositions.

In practical example 13 in particular, the applicant of the present application proposes a novel glycerin derivative-modified silicone (No. 13) having a group that has a siloxane dendron structure, a tetraglycerin derivative group and a diglycerin derivative, and also proposes a water-in-oil emulsion composition containing these (Formulation Example 5) and a W/O emulsion type skin external use preparation (Formulation Example 33). The glycerin derivative-modified silicone proposed here can be used to prepare a stable water-in-oil emulsion when the oil phase is a mixed system of a silicone oil and an organic oil or an oil phase primarily contains an organic oil, and has excellent feeling to touch as a cosmetic composition, but emulsification per se is difficult in a system in which a non-polar organic oil having a relatively high molecular weight, such as a mineral oil, is the primary component of the oil phase, and the emulsion stability, and especially long term emulsion stability at high temperatures, of this system has room for improvement.

As aforementioned, regarding diglycerin-modified silicone, there have been only a few reported cases of application review of emulsifiers for water-in-oil emulsions, and to date only a few with limited structures have been tested. In addition, when compared with ordinary polyether-modified silicones (polyether-based hydrophilic silicone emulsifiers), no glycerin-modified silicones having sufficient emulsification performance with a wide range of oil agents are known as emulsifiers for water-in-oil emulsions. As a result, glycerin-modified silicones, which have a better feeling to touch than polyether-modified silicones and which do not suffer from oxidative degradation due to not having a polyoxyethylene (PEG) structure, could not produce a water-in-oil emulsion cosmetic composition having sufficient stability without additionally using a non-ionic surfactant such as another hydrophilic silicone emulsifier having a PEG structure, and could not achieve the objectives of sufficiently exhibiting a feeling to touch improvement effect as an overall formulation and improving a cosmetic composition to a completely PEG-FREE formulation (a formulation that does not contain a compound having a polyoxyethylene (PEG) structure).

PRIOR ART DOCUMENTS

Non-Patent Documents

Non-Patent Document 1: Y. Kumano, J. Soc. Cosmet. Chem. January, 28, 285 (1977)
Non-Patent Document 2: Michihiro Yamaguchi, J. Soc. Cosmet. Chem. January, 26, 229 (1993) Patent Documents
Patent Document 1: U.S. Pat. No. 4,122,029
Patent Document 2: U.S. Pat. No. 4,268,499
Patent Document 3: U.S. Pat. No. 4,381,241
Patent Document 4: U.S. Pat. No. 4,853,474
Patent Document 5: European Patent No. 176884
Patent Document 6: Japanese Examined Patent Application Publication No. S-62-34039 (Japanese Unexamined Patent Application Publication No. S-57-149290)
Patent Document 7: Japanese Patent No. 2583412 (Japanese Unexamined Patent Application Publication No. S-62-195389)
Patent Document 8: U.S. Pat. No. 4,689,383
Patent Document 9: U.S. Pat. No. 4,908,228 Patent Document 10: Japanese Examined Patent Application Publication No. H-06-089147 (Japanese Patent No. 1956013)
Patent Document 11: Japanese Patent No. 2613124 (Japanese Unexamined Patent Application Publication No. H-04-188795)
Patent Document 12: Japanese Patent No. 2844453 (Japanese Unexamined Patent Application Publication No. H-02-228958)
Patent Document 13: Japanese Patent No. 3389311 (Japanese Unexamined Patent Application Publication No. H-07-238170)
Patent Document 14: Japanese Patent No. 3976226 (Japanese Unexamined Patent Application Publication No. 2002-179798)
Patent Document 15: Japanese Patent No. 4485134 (Japanese Unexamined Patent Application Publication No. 2004-339244)
Patent Document 16: Japanese Unexamined Patent Application Publication No. 2005-042097A
Patent Document 17: Japanese Unexamined Patent Application Publication No. 2005-089494A
Patent Document 18: Japanese Unexamined Patent Application Publication No. 2005-344076A
Patent Document 19: Japanese Unexamined Patent Application Publication No. 2006-218472A
Patent Document 20: Japanese Patent No. 3513682 (Japanese Unexamined Patent Application Publication No. H-09-71504)
Patent Document 21: Japanese Unexamined Patent Application Publication No. H-10-316526
Patent Document 22: Japanese Unexamined Patent Application Publication No. H-10-316527
Patent Document 23: Japanese Unexamined Patent Application Publication No. H-10-316536
Patent Document 24: Japanese Unexamined Patent Application Publication No. H-10-316540
Patent Document 25: Japanese Patent No. 4187198 (WO2002/055588)
Patent Document 26: Japanese Patent No. 3678420 (WO2003/041664)
Patent Document 27: Japanese Unexamined Patent Application Publication No. 2004-169015A
Patent Document 28: Japanese Unexamined Patent Application Publication No. 2004-231605A
Patent Document 29: Japanese Unexamined Patent Application Publication No. 2004-231607A
Patent Document 30: Japanese Unexamined Patent Application Publication No. 2004-231608A
Patent Document 31: WO2011/049248

DISCLOSURE OF INVENTION

Technical Problems

The present invention is to solve the aforementioned problems, and a first objective of the present invention is to provide a novel diglycerin derivative-modified silicone that exhibits particularly excellent emulsification/dispersion properties, especially in cases where the oil phase is the continuous phase. In particular, the first objective of the present invention is to provide a diglycerin derivative-modified silicone which can finely and stably disperse or emulsify an aqueous phase or powder, thereby producing a composition having excellent stability over time or when subjected to heat, not only in cases where the oil phase is a silicone oil, ester oil or triglyceride, but also in cases where the oil phase is a non-polar organic oil such as a mineral oil and isododecane, which was difficult with conventional glycerin-modified silicones.

In addition, a second objective of the present invention is to provide an emulsifier for a water-in-oil emulsion, which contains a diglycerin derivative-modified silicone, which can substantially ameliorate problems caused by oxidative degradation of polyoxyethylene (PEG) due to being able to be designed as a formulation that does not contain a compound having a polyoxyethylene (PEG) structure in a W/O emulsion that contains a variety of oil agents due to exhibiting particularly excellent emulsification performance when the diglycerin derivative-modified silicone is used alone, which can maximize the feeling to touch improvement effect of a W/O emulsion achieved by using the diglycerin derivative-modified silicone. As a result, a W/O emulsion type external use preparation or cosmetic composition having a soft and natural feeling to touch, light smoothness, good spreadability and good moisture retention can be produced.

Furthermore, a third objective of the present invention is to provide a surfactant or dispersing agent which can produce a stable composition having an oil agent as the continuous phase in a wide variety of oil agent systems (a water-in-oil emulsion composition, powder in oil dispersion and the like) due to being a diglycerin derivative-modified silicone having excellent compatibility with a variety of oil agents and emulsification/dispersion properties in an oil agent.

Furthermore, a fourth objective of the present invention is to provide a water-in-oil emulsion composition that contains this type of diglycerin derivative-modified silicone.

Furthermore, a fifth objective of the present invention is to provide an external use preparation or cosmetic composition that contains this type of diglycerin derivative-modified silicone. More specifically, the fifth objective of the present invention is to provide an external use preparation or cosmetic composition that does not contain a compound containing a polyoxyethylene group or polyoxyethylene moiety, that has excellent feeling to touch due to containing the diglycerin derivative-modified silicone according to the present invention, and that is in line with the global trend of improving the constitution of an end consumer product such as a cosmetic product to a completely PEG-FREE formulation.

Solution to Problems

As a result of diligent study, the inventors of the present invention arrived at the present invention, after finding that the aforementioned first problem can be solved by using a diglycerin derivative-modified silicone or a composition that contains the diglycerin derivative-modified silicone, that has a halogen atom-substituted or unsubstituted monovalent hydrocarbon group having 9 to 30 carbons per molecule, that does not have an oxyalkylene structure wherein an average value of the number of repetitions of the oxyalkylene unit is two or more, that has only a glycerin derivative group whose average value of the number of repetitions of glycerin units is within the range from 1.1 to 2.9 as a hydrophilic group, and that does not have other hydrophilic group in the molecule.

In addition, the inventors of the present invention found that it was possible to solve the aforementioned second to fourth problems by means of a surfactant or dispersing agent that contains the diglycerin derivative-modified silicone, and especially an emulsifier for a water-in-oil emulsion and a water-in-oil emulsion composition, and thereby completed the present invention. Furthermore, the inventors of the present invention found that it was possible to solve the aforementioned fifth problem by means of an external use preparation or cosmetic composition which contains these diglycerin derivative-modified silicones and the like and which preferably does not contain a compound having a polyoxyalkylene structure, and thereby completed the present invention.

The inventors of the present invention arrived at the present invention after finding that, when the diglycerin derivative-modified silicone is a diglycerin derivative-modified silicone expressed by the following general formula (1):

the problem can be solved more effectively.

In the general formula (1), $R^1$ is a halogen atom-substituted or unsubstituted monovalent hydrocarbon group having 1 to 8 carbons, alkoxy group, hydrogen atom, or hydroxyl group.

$R^2$ is a halogen atom-substituted or unsubstituted monovalent hydrocarbon group having 9 to 30 carbons.

$R^{Si}$ is a chain organosiloxane group expressed by the following general formula (2-1):

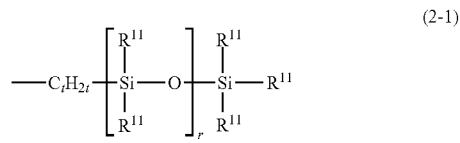

(In the formula, $R^{11}$ are halogen atom-substituted or unsubstituted monovalent hydrocarbon groups having from 1 to 30 carbons, hydroxyl groups, or hydrogen atoms, and at least one of the $R^{11}$ moieties is the monovalent hydrocarbon group; t is a number in a range of 2 to 10; and r is a number in a range of 1 to 500); or the following general formula (2-2):

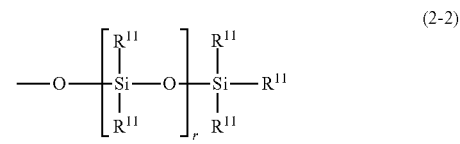

(In the formula, $R^{11}$ and r are synonymous with those described above).

$L^1$ represents a silylalkyl group having the siloxane dendron structure expressed by the following general formula (3) when i=1;

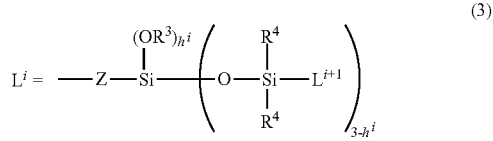

(In the formula, $R^3$ represents a halogen atom-substituted or unsubstituted, straight or branched monovalent hydrocarbon group having 1 to 30 carbons; $R^4$ each independently represents a phenyl group or an alkyl group having from 1 to 6 carbons; Z represents a divalent organic group; i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^4$ moiety when i=k; and $h^i$ is a number in a range of 0 to 3).

Q is a glycerin derivative group having an average value of the number of repetitions of a glycerin unit of 1.1 to 2.9, and "a," "b," "c," "d," and "e," are values within the ranges $1.0 \le a \le 2.5$, $0 < b \le 1.5$, $0 \le c+d \le 1.5$, and $0.001 \le e \le 1.5$.

That is, the aforementioned objectives can be achieved by:

"[1] A diglycerin derivative-modified silicone that has a halogen atom-substituted or unsubstituted monovalent hydrocarbon group having 9 to 30 carbons per molecule, that does not have an oxyalkylene structure wherein an average value of the number of repetitions of the oxyalkylene unit is two or more, that has only a glycerin derivative group whose average value of the number of repetitions of glycerin units is within the range from 1.1 to 2.9 as a hydrophilic group, and that does not have other hydrophilic group in a molecule.

[2] The diglycerin derivative-modified silicone described in [1], wherein the other hydrophilic group is an oxyalkylene derivative group having an oxyalkylene structure wherein an average value of the number of repetitions of the oxyalkylene unit is two or more or a (poly)glycerin derivative group, excluding a glycerin derivative group having an average value of the number of repetitions of glycerin units within the range from 1.1 to 2.9.

[3] The diglycerin derivative-modified silicone described in [1] or [2], wherein, in the glycerin derivative group, the average value of the number of repetitions of glycerin units is within the range from 1.5 to 2.4.

[4] The diglycerin derivative-modified silicone described in any of [1] to [3] expressed by the following general formula (1):

$$R^1{}_a R^2{}_b R^{Si}{}_c L^1{}_d Q_e SiO_{(4-a-b-c-d-e)/2} \quad (1)$$

In the general formula (1), $R^1$ is a halogen atom-substituted or unsubstituted monovalent hydrocarbon group having 1 to 8 carbons, alkoxy group, hydrogen atom, or hydroxyl group.

$R^2$ is a halogen atom-substituted or unsubstituted monovalent hydrocarbon group having 9 to 30 carbons.

$R^{Si}$ is a chain organosiloxane group expressed by the following general formula (2-1):

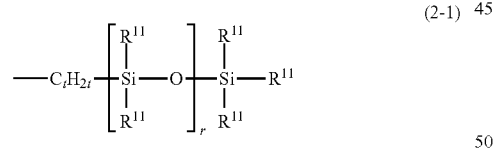

(In the formula, $R^{11}$ are halogen atom-substituted or unsubstituted monovalent hydrocarbon groups having from 1 to 30 carbons, hydroxyl groups, or hydrogen atoms, and at least one of the $R^{11}$ moieties is the monovalent hydrocarbon group; t is a number in a range of 2 to 10; and r is a number in a range of 1 to 500); or the following general formula (2-2):

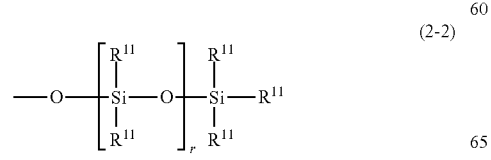

(In the formula, $R^{11}$ and r are synonymous with those described above).

$L^1$ represents a silylalkyl group having the siloxane dendron structure expressed by the following general formula (3) when i=1;

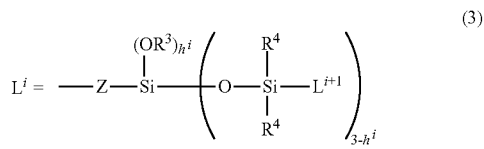

(In the formula, $R^3$ represents a halogen atom-substituted or unsubstituted, straight or branched monovalent hydrocarbon group having 1 to 30 carbons; $R^4$ each independently represents a phenyl group or an alkyl group having from 1 to 6 carbons; Z represents a divalent organic group; i represents a generation of the silylalkyl group represented by and is an integer of 1 to k when k is a number of generations that is a number of repetitions of the silylalkyl group; the number of generations k is an integer from 1 to 10; $L^{i+1}$ is the silylalkyl group when i is less than k, and the $R^4$ moiety when i=k; and $h^i$ is a number in a range of 0 to 3).

Q is a glycerin derivative group having an average value of the number of repetitions of a glycerin unit of 1.1 to 2.9, and "a," "b," "c," "d," and "e," are values within the ranges $1.0 \le a \le 2.5$, $0 < b \le 1.5$, $0 \le c+d \le 1.5$, and $0.001 \le e \le 1.5$.

[5] The diglycerin derivative-modified silicone described in any of [1] to [4], wherein the glycerin derivative group is a diglycerin derivative group-containing organic group which is bonded to silicon atoms via a linking group that is at least divalent, and which has an average value of the number of repetitions of a glycerin unit of 1.5 to 2.4 of one or more glycerin units selected from among the hydrophilic units represented by structural formulae (4-1) to (4-3) below (but which does not comprise an oxyalkylene structure wherein an average value of the number of repetitions of the oxyalkylene unit is two or more in the same functional group).

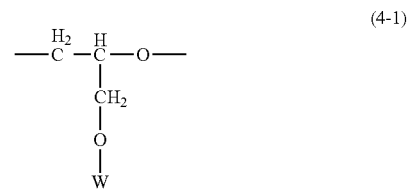

(In this formula, W is a hydrogen atom or an alkyl group having from 1 to 20 carbons)

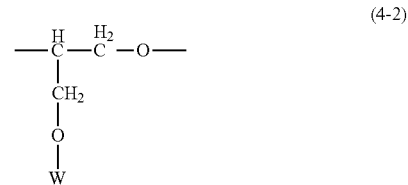

(In this formula, W is synonymous with the group described above).

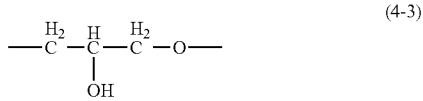

(4-3)

[6] A composition comprising the diglycerin derivative-modified silicone described in any one of [1] to [5], wherein the glycerin derivative group is a diglycerin derivative group-containing organic group expressed by the following general formula (5-1):

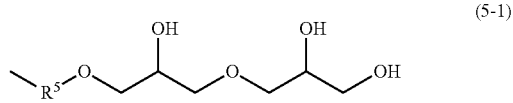

(5-1)

(In the formula, $R^5$ is a divalent organic group that does not comprise an oxyalkylene structure wherein an average value of the number of repetitions of the oxyalkylene unit is two or more) or the following general formula (5-2):

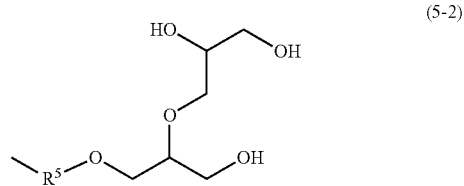

(5-2)

(In the formula, $R^5$ is synonymous with that described above).

[7] The diglycerin derivative-modified silicone described in any one of [1] to [6] represented by the structural formula (1-1) below:

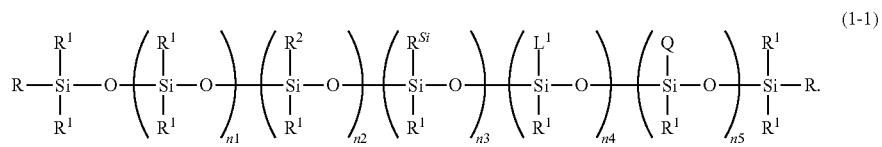

(1-1)

In the formula, $R^1$, $R^2$, $R^{Si}$, $L^1$ and Q are synonymous with the groups described above; and R are selected from among $R^1$, $R^2$, $R^{Si}$, $L^1$, and Q. However, when n2=0, at least one R is $R^2$, and when n5=0, at least one R is Q. (n1+n2+n3+n4+n5) is a number in a range from 1 to 200; n1 is a number in a range from 0 to 100; n2 is a number in a range from 0 to 100; n3 is a number in a range from 0 to 20; n4 is a number in a range from 0 to 20; and n5 is a number in a range from 0 to 20.

[8] A composition comprising the diglycerin derivative-modified silicone described in any one of [1] to [7].

[9] A surfactant or dispersing agent comprising the diglycerin derivative-modified silicone described in any one of [1] to [7] or the composition described in [8].

[10] The surfactant or dispersing agent described in [9], which is used to prepare a composition having an oil agent as a continuous phase.

[11] The surfactant described in [9] or [10], which is an emulsifier for a water-in-oil emulsion.

[12] A water-in-oil emulsion composition comprising the diglycerin derivative-modified silicone described in any one of [1] to [7] or the composition described in [8].

[13] A water-in-oil emulsion composition comprising: (A) the diglycerin derivative-modified silicone described in any one of [1] to [7] or the composition described in [8], (B) water, and (C) at least one type of oil agent that is liquid at 5 to 100° C. selected from among the group comprising silicone oils, non-polar organic compounds and lowly to highly polar organic compounds.

[14] The water-in-oil emulsion composition described in [12] or [13], that does not comprise a compound having an oxyalkylene structure wherein an average value of the number of repetitions of the oxyalkylene unit is two or more.

[15] An external use preparation or cosmetic composition comprising the diglycerin derivative-modified silicone described in any one of [1] to [7] or the composition described in [8].

[16] An external use preparation or a cosmetic composition comprising the water-in-oil emulsion composition described in any one of [12] to [14].

[17] The external use preparation or cosmetic composition described in [15] or [16], which is in the form of a water-in-oil emulsion.

[18] The external use preparation or cosmetic composition described in any one of [15] to [17], that does not comprise a compound having an oxyalkylene structure wherein an average value of the number of repetitions of the oxyalkylene unit is two or more."

Advantageous Effects of Invention

According to the present invention, it is possible to provide a novel diglycerin derivative-modified silicone that exhibits particularly excellent emulsification/dispersion properties in cases where the oil phase is the continuous phase. In particular, the diglycerin derivative-modified silicone of the present invention or the composition containing the same can finely and stably emulsify/disperse an aqueous phase or powder not only in cases where the oil phase is a silicone oil, ester oil or triglyceride, but also in cases where the oil phase is a non-polar organic oil such as a mineral oil, isododecane and the like, which was difficult with conventional glycerin-modified silicones. Therefore, the diglycerin derivative-modified silicone of the present invention or the composition containing the same can produce a composition having excellent stability over time or when subjected to heat, can stably emulsify/disperse an aqueous phase or powder in a wide variety of oil agent systems without using a PEG-containing compound such as a polyether-modified silicone, can obtain a composition having excellent stability over time or when subjected to heat, and can therefore improve the constitution of an end consumer product, such as an external use preparation and cosmetic product, to a completely PEG-FREE formulation, which has high environmental suitability.

By using the diglycerin derivative-modified silicone of the present invention or a composition containing the same, it is possible to design a formulation not containing a compound having a polyoxyethylene (PEG) structure, and it is therefore possible to substantially ameliorate problems caused by oxidative degradation of polyoxyethylene (PEG) and maximize the feeling to touch improvement effect of a W/O emulsion achieved by using a diglycerin derivative-modified silicone. As a result, it is possible to provide an emulsifier for a water-in-oil emulsion that contains a diglycerin derivative-modified silicone capable of providing a W/O emulsion type external use preparation or cosmetic composition having a soft and natural feeling to touch, light smoothness, good spreadability and good moisture retention.

Furthermore, by using the diglycerin derivative-modified silicone of the present invention or composition containing the same, it is possible to provide a surfactant or dispersing agent that can produce a stable composition having an oil agent as the continuous phase in a wide variety of oil agent systems (a water-in-oil emulsion composition, a polyol-in-oil type emulsion composition, a polar solvent-in-oil type emulsion composition or a powder in oil dispersion).

Furthermore, by using the diglycerin derivative-modified silicone of the present invention or composition containing the same, it is possible to maximize the feeling to touch improvement effect of a W/O emulsion achieved by using the diglycerin derivative-modified silicone and provide a water-in-oil emulsion composition having excellent stability over time.

Furthermore, by using the diglycerin derivative-modified silicone of the present invention or composition containing the same, it is possible to provide an external use preparation or cosmetic composition that does not contain a compound containing a polyoxyethylene group or polyoxyethylene moiety, that has excellent feeling to touch, and that is in line with the global trend of improving the constitution of an end consumer product such as a cosmetic product to a completely PEG-FREE formulation.

DESCRIPTION OF EMBODIMENTS

Detailed explanations will now be given of the diglycerin derivative-modified silicone according to the present invention and use thereof as a surfactant or dispersing agent, and especially use as an emulsifier for a water-in-oil emulsion. In addition, a detailed explanation will be given of an external use preparation or cosmetic composition that contains the diglycerin derivative-modified silicone of the present invention, and especially an external use preparation or cosmetic composition that does not contain a compound having a polyoxyalkylene structure.

Furthermore, the diglycerin derivative-modified silicone of the present invention and a composition containing the same can be used in the same intended uses as those of the co-modified organopolysiloxane disclosed in the aforementioned Patent Document 31 (WO 2011/049248). The diglycerin derivative-modified silicone of the present invention and a composition containing the same can be used as a surfactant (emulsifier) or a variety of treatment agents (powder dispersing agent or surface treatment agent), can be used in particular as an emulsifier or a powder treatment agent or as a cosmetic raw material, can be combined with an arbitrary cosmetic raw material component, can be used in the same way as the co-modified organopolysiloxanes disclosed in the Patent Document 31 in external use preparations, and especially in formulations, types and formulation examples of cosmetic compounds, and can be blended in a variety of cosmetic compositions. The diglycerin derivative-modified silicone according to the present invention has excellent feeling to touch and, when used alone, exhibits particularly excellent capability for stably emulsifying/dispersing an aqueous phase or stably dispersing a powder in a wide variety of oil agents, and therefore forms an external use preparation or cosmetic composition having the advantages of further increasing the flexibility of formulations of external use preparations and cosmetic compositions, improving the cosmetic effects, having further improved stability over time and feeling to touch, and which is, if necessary, improved to a PEG-FREE formulation in the various intended uses of the co-modified organopolysiloxanes disclosed in the aforementioned Patent Document 31.

The diglycerin derivative-modified silicone according to the present invention, or the composition comprising the same is particularly superior as a surfactant, an emulsifier, or a (powder) dispersing agent, but also is effective as a tactile sensation improver, a moisturizing agent, a binder, a surface treatment agent, and a skin adhesive. Additionally, the diglycerin derivative-modified silicone according to the present invention, or the composition comprising the same can be combined with water in order to function as a film agent or a viscosity adjusting agent.

The diglycerin derivative-modified silicone of the present invention or a composition containing the same contains a long chain alkyl group as a lipophilic group in a molecule, does not have an oxyalkylene structure wherein an average value of the number of repetitions of the oxyalkylene unit is two or more as a hydrophilic group, has only a glycerin derivative group with an average value of the number of repetitions of glycerin units of 1.1 to 2.9 (more preferably 1.5 to 2.4), and does not have other hydrophilic group in the molecule. That is, the diglycerin derivative-modified silicone of the present invention contains a long chain hydrocarbon group within a molecule, and contains mainly a diglycerin derivative group as the hydrophilic group.

As a result, emulsification performance when used alone is superior to that of publicly known (poly)glycerin-modified silicones, and it is possible to design a formulation that does not contain a compound having a polyoxyethylene (PEG) structure, and it is therefore possible to substantially ameliorate problems caused by oxidative degradation of polyoxyethylene (PEG).

The first feature of the diglycerin derivative-modified silicone of the present invention is that the diglycerin derivative-modified silicone contains a long chain hydrocarbon group within a molecule, contains mainly a diglycerin derivative group as a hydrophilic group, and does not have a polyoxyalkylene group or other hydrophilic group or a hydrophilic structure in the molecule.

First, the long chain hydrocarbon group in the diglycerin derivative-modified silicone molecule of the present invention will be described. The diglycerin derivative-modified silicone of the present invention has a halogen atom-substituted or unsubstituted monovalent hydrocarbon group with 9 to 30 carbons in the molecule. Such a long chain hydrocarbon group is introduced into a molecule together with a hydrophilic group consisting mainly of a diglycerin derivative group mentioned later. As a result, the glycerin derivative modified silicone of the present invention exhibits compatibility superior not only to silicone oil, but also to non silicone oils containing a large number of alkyl groups. For example, it is possible to obtain an emulsion and dispersed substance that are composed of a non silicone oil and exhibit superior thermal stability and stability over time.

As a result, the emulsification performance for an oil agent, when the diglycerin derivative-modified silicone is used alone, is markedly improved over those of publicly known (poly)glycerin-modified silicones, thereby yielding an emulsification performance that is high enough to enable the design of formulations not containing a compound having a polyoxyethylene (PEG) structure.

A halogen atom-substituted or unsubstituted monovalent hydrocarbon group with 9 to 30 carbons is at least one type of long chain monovalent hydrocarbon group, and 2 or more types of monovalent hydrocarbon groups with different quantities of carbons may be contained in the molecule. Furthermore, their structure is selected from among straight chain, branched, and partially branched. In the present invention, it is particularly preferable for $R^2$ to be an unsubstituted straight chain monovalent hydrocarbon group. An unsubstituted monovalent hydrocarbon group can be, for example, an alkyl group, aryl group or aralkyl group having 9 to 30 carbons, and more preferably 10 to 24 carbons. Meanwhile, a halogen atom-substituted monovalent hydrocarbon group can be, for example, a perfluoroalkyl group having 9 to 30 carbons, and more preferably 10 to 24 carbons. This type of monovalent hydrocarbon group is particularly preferably an alkyl group having 9 to 30 carbons, and an example thereof is a group represented by the general formula —$(CH_2)_v$—$CH_3$ (v is a number in a range of 8 to 29). Particularly, an alkyl group having 10 to 24 carbons is preferable. In particular, by having an alkyl group with 10 to 24 carbons, compatibility with non silicone oils containing a large number of alkyl groups is improved, and emulsification performance of the diglycerin derivative-modified silicone of the present invention or a composition containing the same is further improved.

The diglycerin derivative-modified silicone of the present invention contains the long chain hydrocarbon group in a molecule, does not have an oxyalkylene structure wherein an average value of the number of repetitions of the oxyalkylene unit is two or more, has only a glycerin derivative group with an average value of the number of repetitions of glycerin units of 1.1 to 2.9 (more preferably 1.5 to 2.4) as a hydrophilic group, and does not have other hydrophilic group in the molecule. Furthermore, a hydrophilic group or hydrophilic structure indicates a functional group or a molecular structure that imparts hydrophilicity to a silicone molecule, and generally is a functional group or a structure derived from a hydrophilic compound.

In particular, in the present invention, it is essential to satisfy the condition that the average value of the number of repetitions of glycerin units in a molecule is in a range from 1.1 to 2.9, and if a glycerin derivative group does not satisfy the condition, it is not preferable because the emulsification performance drops. Furthermore, in the present invention, an oxyalkylene derivative group containing an oxyalkylene structure wherein an average value of the number of repetitions of the oxyalkylene unit is two or more in a molecule, or a structure similar thereto, must not be present as a hydrophilic group. In particular, if a polyoxyalkylene-modified group containing a polyoxyalkylene structure or a structure similar thereto is present in the molecule as a hydrophilic group, it is not possible to achieve the objective of the present invention, that is, substantially improving the problem of oxidative degradation of polyoxyethylene (PEG). In addition, if the polyoxyalkylene-modified group is contained in the molecule, it is impossible to suppress the oiliness, stickiness, or the like of a cosmetic composition, and especially a water-in-oil type emulsion cosmetic composition, that contains polyoxyalkylene-modified group and the feeling to touch of the composition can significantly deteriorate compared to a case in which only a glycerin derivative group is contained as a hydrophilic group.

The second feature of the diglycerin derivative-modified silicone of the present invention is that the diglycerin derivative-modified silicone has a diglycerin derivative group as a hydrophilic group in the molecule. In the diglycerin derivative group, the average value of the number of repetitions of the glycerin unit is in a range from 1.1 to 2.9, and the average value of the number of repetitions is preferably in a range from 1.5 to 2.4, more preferably in a range from 1.8 to 2.2, and most preferably an average of 2. In addition, if the average value of the number of repetitions of a glycerin unit is less than the lower limit or exceeds the upper limit, the emulsification/dispersion performance of the glycerin derivative-modified silicone deteriorates, it is particularly difficult to disperse in an oil phase that contains an organic oil, and it is not possible to obtain a water-in-oil emulsion composition that is stable over a long period of time.

The number of repetitions of the glycerin unit may be an average value. A content of the diglycerin derivative group in which the number of repetitions of the glycerin unit is 2 is preferably more than 30 wt. %, more preferably 50 wt. % or more, and even more preferably 80 wt. % or more, with respect to all of the other glycerin derivative groups. Most preferable is a pure form in which purity of the diglycerin derivative group is greater than 98 wt. %. That is, the diglycerin derivative-modified silicone of the present invention has an average value of the number of repetitions of a glycerin unit that falls within the aforementioned range, and may be a hydrophilic group that contains mainly a group in which the average value of the number of repetitions is 2, or may be a hydrophilic group that contains only a high purity diglycerin moiety. Meanwhile, a glycerin derivative-modified silicone mixture such as one obtained by blending a refined triglycerin ddrivative-modified silicone, in which the number of repetitions of a glycerin unit is 3, and a monoglycerin derivative-modified silicone, in which the number of repetitions of a glycerin unit is 1, at a mass ratio of 1:1 exhibits poor emulsification/dispersion performance, and cannot therefore be advantageously used in the diglycerin derivative-modified silicone according to the present invention.

This type of diglycerin derivative group is preferably a diglycerin derivative group-containing organic group which is bonded to a silicon atom via a linking group that is at least divalent and which contains an average of 1.5 to 2.4 of one or more glycerin units selected from among the hydrophilic units represented by structural formulae (4-1) to (4-3) below (but which does not contain an oxyalkylene structure wherein an average value of the number of repetitions of the oxyalkylene unit is two or more in the same functional group). Note that the preferable range of the number of repetitions of each glycerin unit is the same as that described above.

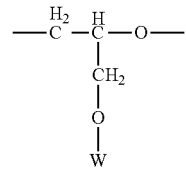

(4-1)

(In this formula, W is a hydrogen atom or an alkyl group having from 1 to 20 carbons)

(4-2)

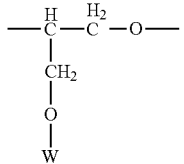

(In this formula, W is synonymous with the group described above).

(4-3)

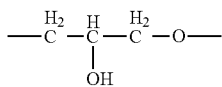

In the formulae (4-1) to (4-3), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The diglycerin derivative group has an average value of the number of repetitions of a glycerin unit of 1.5 to 2.4, and more preferably 2, and preferably does not contain a branch in the glycerin unit repeating structure, but it is possible for a part of the structure to be branched, such as a part of the structure being a polyglycerol group or a polyglycidyl ether group.

The divalent linking group is contained in the diglycerin derivative group, is a bonding site to a silicon atom, and is a divalent organic group that does not contain an oxyalkylene structure wherein an average value of the number of repetitions of the oxyalkylene unit is two or more. Specifically, the divalent linking group is a straight chain or branched chain alkylene group such as an ethylene group, propylene group, butylene group or hexylene group; an alkylene phenylene group such as an ethylene phenylene group or a propylene phenylene group; an alkylene aralkylene group such as an ethylene benzylene group; an alkylenoxyphenylene group such as an ethylenoxyphenylene group or a propylenoxyphenylene group; or an alkylenoxybenzylene group such as a methylenoxybenzylene group, ethylenoxybenzylene group or propylenoxybenzylene group. The divalent linking group is most preferably selected from among the divalent organic groups represented by the general formulae below.

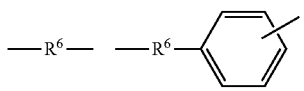

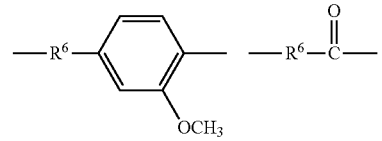

(In these formulae, $R^6$ may have a substituent, and are each independently a straight or branched chain alkylene group or alkenylene group having from 2 to 22 carbons, or an arylene group having from 6 to 22 carbons)

The diglycerin derivative group is more preferably a diglycerin derivative group represented by structural formula (5) below:

$$—R^5—O—X_m—H \qquad (5)$$

In the formula, $R^5$ is a divalent organic group that does not contain an oxyalkylene structure wherein an average value of the number of repetitions of the oxyalkylene unit is two or more, and examples thereof include groups similar to the aforementioned divalent linking groups. X is at least one type of glycerin unit selected from the hydrophilic units represented by the structural formulae (4-1) to (4-3). m represents the number of repetitions of the glycerin unit, and is on average, a number in a range from 1.5 to 2.4. Note that the preferable range of the number of repetitions of each glycerin unit is the same as that described above.

It is most preferable for the diglycerin derivative group-containing organic group to be a diglycerin derivative group-containing organic group represented by following general formula (5-1):

(5-1)

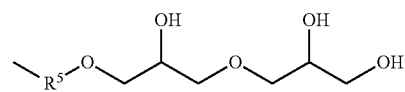

(In the formula, $R^5$ is a divalent organic group that does not contain an oxyalkylene structure wherein an average value of the number of repetitions of the oxyalkylene unit is two or more) or the following general formula (5-2):

(5-2)

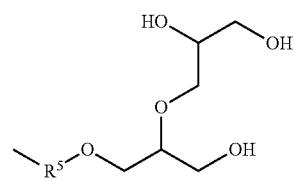

(wherein $R^5$ is synonymous with that described above).

In the diglycerin derivative-modified silicone according to the present invention, the diglycerin derivative group-containing organic group is preferably a hydrophilic group derived from diglycerin monoallyl ether or diglyceryl eugenol.

The bond position of the diglycerin derivative group-containing organic group can be either the terminal or side chain of polysiloxane, which is main chain, and one molecule of a diglycerin derivative-modified silicone can have a structure having two or more diglycerin derivative group-containing organic groups. The diglycerin derivative-modified silicone preferably has two or more diglycerin derivative group-containing organic groups. Furthermore, these two or more diglycerin derivative group-containing organic groups can be structured such that bonding occurs only in a side chain of polysiloxane, which is the main chain, only at a terminal, or in a side chain and at a terminal.

In the diglycerin derivative-modified silicone of the present invention, which has only a diglycerin derivative-containing organic group as the long chain monovalent hydrocarbon group and hydrophilic group, polysiloxane main chain thereof may have a straight chain, branched chain or silicone resin structure, and, as long as the objective of the present invention is not impaired, the diglycerin derivative-modified silicone of the present invention may be a diglycerin derivative-modified silicone that has been further modified by an organic group other than a long chain monovalent hydrocarbon group or hydrophilic group, such as an organic group including an alkoxy group, (meth)acryl group, epoxy group, acyl group, ester group, and mercapto group. However, the diglycerin derivative-modified silicone of the present invention preferably is a co-modified diglycerin derivative-modified silicone expressed by the following general formula (1).

General Formula (1):

$$R^1_a R^2_b R^{Si}_c L^1_d Q_e SiO_{(4-a-b-c-d-e)/2} \quad (1)$$

In the general formula (1),
$R^1$ is a halogen atom-substituted or unsubstituted monovalent hydrocarbon group having 1 to 8 carbons, alkoxy group, hydrogen atom, or hydroxyl group. $R^2$ is a halogen atom-substituted or unsubstituted monovalent hydrocarbon group having 9 to 30 carbons.
$R^{Si}$ is a chain organosiloxane group expressed by the general formula (2-1) below:

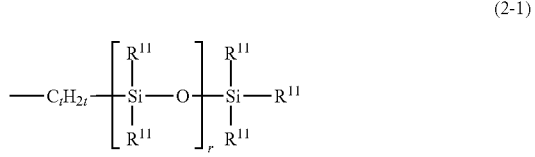

(2-1)

(In the formula, $R^{11}$ are halogen atom-substituted or unsubstituted monovalent hydrocarbon groups having from 1 to 30 carbons, hydroxyl groups, or hydrogen atoms, and at least one of the $R^{11}$ moieties is the monovalent hydrocarbon group; t is a number in a range of 2 to 10; and r is a number in a range of 1 to 500); or the following general formula (2-2):

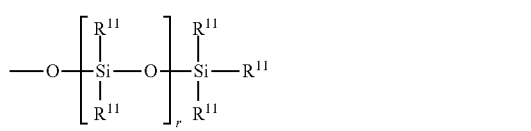

(2-2)

(In the formula, $R^{11}$ and r are synonymous with those described above)
$L^1$ represents a silylalkyl group having the siloxane dendron structure expressed by the following general formula (3) when i=1;

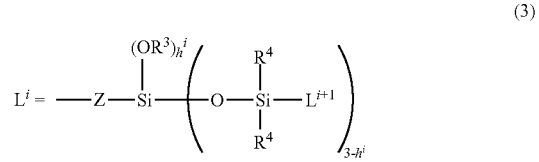

(3)

(In the formula, $R^3$ represents a halogen atom-substituted or unsubstituted, straight or branched monovalent hydrocarbon group having 1 to 30 carbons; $R^4$ each independently represents a phenyl group or an alkyl group having from 1 to 6 carbons; Z represents a divalent organic group; i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^4$ moiety when i=k; and $h^i$ is a number in a range of 0 to 3).

Q is a glycerin derivative group having an average value of the number of repetitions of a glycerin unit of 1.1 to 2.9, and "a," "b," "c," "d," and "e," are values within the ranges $1.0 \le a \le 2.5$, $0 < b \le 1.5$, $0 \le c+d \le 1.5$, and $0.001 \le e \le 1.5$.

In the diglycerin derivative-modified silicone of the present invention, expressed by general formula (1), the long chain monovalent hydrocarbon group represented by the $R^2$ is an essential substituted group, "b" is greater than 0 and is a number within the range $0 < b \le 1.5$. Particularly, from the standpoint of improving the emulsifiability of a non silicone based oil agent, "b" is preferably $0.0001 \le b \le 1.5$, and is more preferably $0.001 \le b \le 1.5$.

Similarly, the diglycerin derivative-modified silicone of the present invention can have a chain organosiloxane group represented by the $R^{Si}$ and/or a silylalkyl group having a siloxane dendron structure represented by the $L^1$. As a result of having these functional groups, in the diglycerin derivative-modified silicone of the present invention, these functional groups are any functional group, and c+e is a number greater than or equal to 0. On the other hand, when these functional groups exist within a molecule, c+d is a number greater than 0, preferably $0.0001 \le c+d \le 1.5$, and more preferably $0.001 \le c+d \le 1.5$.

At this point, the preferable values of c and d satisfy the relationship $0.001 \le c+d \le 1.5$, and are expressed as follows by using the functional group considered to be essential in. the molecule.
(1) When there is a group represented by $R^{Si}$: $0.001 \le c \le 1.5$ and $0 \le d \le 1.5$.
(2) When there is a group represented by $L^1$: $0 \le c \le 1.5$ and $0.001 \le d \le 1.5$.
(3) When there are both a group represented by $R^{Si}$ and a group represented by $0.001 \le c \le 1.5$ and $0.001 \le d \le 1.5$.

$R^1$ in the general formula (1) is a halogen atom-substituted or unsubstituted monovalent hydrocarbon group having 1 to 8 carbons, alkoxy group, hydrogen atom, or hydroxyl group.

Examples of the monovalent hydrocarbon group with 1 to 8 carbons include alkyl groups such as a methyl group, ethyl group, propyl group, butyl group, pentyl group, hexyl group, heptyl group, and octyl group; cycloalkyl groups such as a cyclopentyl group, and cyclohexyl group; alkenyl groups such as a vinyl group, allyl group, and butenyl group; aryl groups such as a phenyl group, and tolyl group; aralkyl group such as benzyl group; and groups wherein the hydrogen atoms bonded to the carbon atoms of these groups are substituted at least partially by fluorine or a similar halogen atom (provided that the total number of carbons is from 1 to 8). The monovalent hydrocarbon group is preferably a group other than an alkenyl group, and is more preferably a methyl group, an ethyl group, or a phenyl group. Also, the alkoxy group is exemplified by a methoxy group, an ethoxy group, an isopropanoxy group, a higher alkoxy group, and the like.

Particularly, the $R^1$ moieties are preferably monovalent hydrocarbon groups having from 1 to 8 carbons and that are free of unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is a methyl group, an ethyl group, or a phenyl group, and more preferably from 90 mol % to 100 mol % of all the $R^1$ moieties are selected from methyl groups, ethyl groups, or phenyl groups.

$R^2$ of general formula (1) is a halogen atom-substituted or unsubstituted monovalent hydrocarbon group with 9 to 30 carbons, and is exemplified by and is preferably synonymous with the groups described above.

The groups represented by $R^{Si}$ of the general formula (1) are the chain organosiloxane groups expressed by the general formula (2-1) or (2-2). By introducing the chain organosiloxane group into the main chain and/or side chain of polysiloxane, it is possible to adjust the affinity, dispersion stability, and sensation during use of various components such as an oil agent, and powder, combined in an external use preparation or a cosmetic composition. This is particularly useful in that the compatibility and compounding stability with a silicone oil is further improved by having in the molecule a chain organopolysiloxane group represented by $R^{Si}$.

The chain organosiloxane group in general formula (2-1) or (2-2) has a straight chain polysiloxane chain structure, unlike a silylalkyl group, which has a siloxane dendron structure. In general formula (2-1) or (2-2), $R^{11}$ are each independently a halogen atom-substituted or unsubstituted monovalent hydrocarbon group having from 1 to 30 carbons, a hydroxyl group or a hydrogen atom. The halogen atom-substituted or unsubstituted monovalent hydrocarbon group with 1 to 30 carbon atoms is preferably an alkyl group with 1 to 30 carbon atoms, an aryl group with 6 to 30 carbon atoms, an aralkyl group with 6 to 30 carbon atoms, or a cycloalkyl group with 6 to 30 carbon atoms, and is exemplified by a methyl group, ethyl group, propyl group, butyl group, pentyl group, hexyl group, heptyl group, octyl group, decyl group or other alkyl group; a cyclopentyl group, cyclohexyl group or other cycloalkyl group; a phenyl group, tolyl group or other aryl group; or groups wherein the hydrogen atoms bonded to the carbon atoms of these groups may be substituted at least partially by fluorine or a similar halogen atom. Particularly suitable as $R^{11}$ is a methyl group, a phenyl group or a hydroxyl group. Also suitable is a configuration in which a part of $R^{11}$ is a methyl group and another part of $R^{11}$ is a long chain alkyl group having 8 to 30 carbon atoms.

In general formula (2-1) or (2-2), t is a number in a range from 2 to 10; r is a number in a range from 1 to 500; and r preferably is a number in a range from 2 to 500. Such a straight chain organosiloxane group is hydrophobic. From the standpoint of compatibility with various oil agents, r preferably is a number in a range from 1 to 100, and particularly preferably is a number in a range from 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the diglycerin derivative-modified silicone is used, the silylalkyl group inhibits the unpleasant sticky feeling, and provides a superior smoothness and refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the halogen atom-substituted or unsubstituted, straight or branched monovalent hydrocarbon group having 1 to 30 carbon atoms (the $R^3$ moieties in the general formula (3)) include methyl groups, ethyl groups, propyl groups, butyl groups, pentyl groups, hexyl groups, heptyl groups, octyl groups, and similar alkyl group; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom Among the phenyl group or the alkyl group having from 1 to 6 carbons represented by $R^4$ in general formula (3), examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In general formula (3), in the case of i=k, $R^4$ is preferably a methyl group or a phenyl group. In particular, $R^4$ is preferably a methyl group when i=k.

From a technical standpoint, the number of generations k is preferably an integer from 1 to 3, and more preferably is 1 or 2. In each of the number of generations, the group represented by $L^1$ is represented as follows. In the formulae, $R^3$, $R^4$, and Z are the same groups as described above.

When the number of generations is k=1, $L^1$ is expressed by the following general formula (3-1).

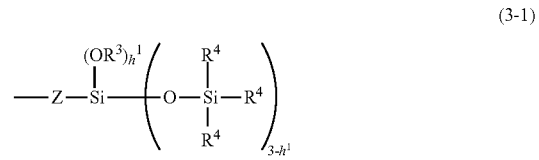

(3-1)

When the number of generations is k=2, $L^1$ is expressed by the following general formula (3-2).

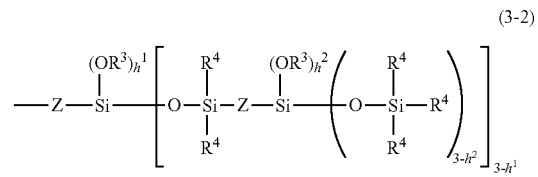

(3-2)

When the number of generations is k=3, $L^1$ is expressed by the following general formula (3-3).

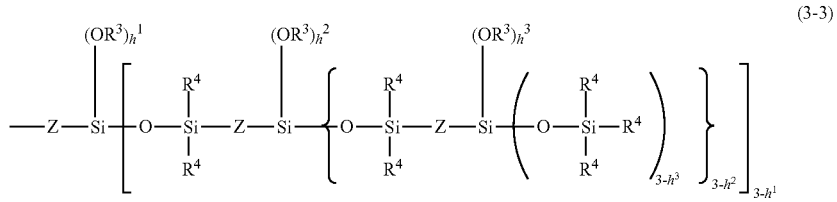

(3-3)

In the structures expressed by the general formulae (3-1) to (3-3) in the case of the number of generations is from 1 to 3, each of $h^1$, $h^2$ and $h^3$ moieties is independently a number in a range from 0 to 3. These $h^i$ moieties are preferably a number in a range from 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. In the present invention, however, groups containing an oxyalkylene structure wherein an average value of the number of repetitions of the oxyalkylene unit is two or more cannot be used and are not preferable.

Preferably, Z are each independently a group selected from divalent organic groups expressed by the following general formula.

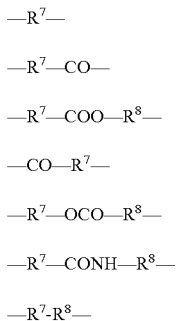

Of these, Z in $L^1$ is preferably a divalent organic group expressed by general formula $—R^7—$ that is introduced by a reaction between a silicon-bonded hydrogen atom and an alkenyl group. Likewise, Z is preferably a divalent organic group expressed by general formula $—R^7—COO—R^8—$ that is introduced by a reaction between a silicon-bonded hydrogen atom and an unsaturated carboxylic ester group. On the other hand, in the silylalkyl group represented by $L^i$, in which the number of generations k is 2 or more, and $L^i$ is $L^2$ to $L^k$, Z is preferably an alkylene group having 2 to 10 carbons and, in particular, is preferably a group selected from an ethylene group, a propylene group, a methylethylene group and a hexylene group, and most preferably is an ethylene group.

In the general formula described above, $R^7$ are each independently a substituted or unsubstituted straight or branched chain alkylene group or alkenylene group having from 2 to 22 carbons or an arylene group having from 6 to 22 carbons. More specifically, examples of $R^7$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^7$ is preferably a group selected from an ethylene group, a propylene group, a methylethylene group, and a hexylene group.

In the general formula described above, $R^8$ is a group selected from divalent organic groups expressed by the following formula.

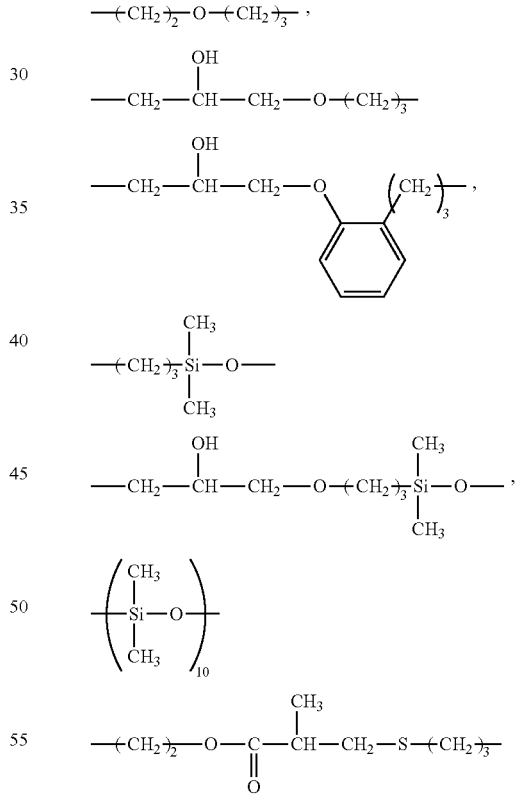

In general formula (1), Q is a glycerin derivative group having an average value of the number of repetitions of a glycerin unit of 1.1 to 2.9, and forms the hydrophilic site of the diglycerin derivative-modified silicone. Q is exemplified by and preferably selected from among the aforementioned hydrophilic groups.

The particularly preferable diglycerin derivative-modified silicone of the present invention is a diglycerin derivative-modified silicone having a straight chain polysiloxane structure represented by structural formula (1-1) below:

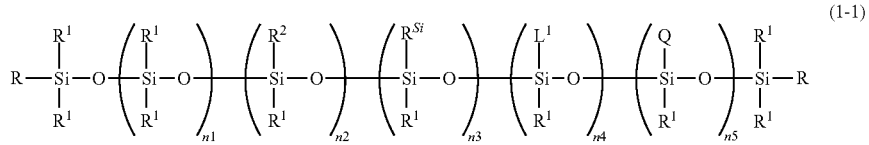

(1-1)

In the formula, $R^1$, $R^2$, $L^1$, and Q are synonymous with the groups described above; and R are selected from among $R^1$, $R^2$, $R^{Si}$, $L^1$, and Q. However, when n2=0, at least one R is $R^2$, and when n5=0, at least one R is Q. (n1+n2+n3+n4+n5) is a number in a range from 1 to 200; n1 is a number in a range from 0 to 100; n2 is a number in a range from 0 to 100; n3 is a number in a range from 0 to 20; n4 is a number in a range from 0 to 20; and n5 is a number in a range from 0 to 20. The diglycerin derivative-modified silicone of the present invention is particularly preferably a diglycerin derivative-modified silicone having the straight chain polymethylsiloxane structure represented by the following structural formula (1-1A), wherein all $R^1$ are methyl groups.

n4 is preferably a number in a range from 0 to 20. It is particularly preferable that n4>1 and the diglycerin derivative-modified silicone has at least one silylalkyl group (-$L^1$) having a siloxane dendron structure in a side chain portion, and it is preferable that n4 is within the range of 1 to 10.

n5 is a number in a range from 0 to 20, and preferably in a range from 1 to 10. However, when n5=0, at least one X must be Q.

In the structural formula (1-1A), Q is a glycerin derivative group having an average value of the number of repetitions of glycerin unit of 1.1 to 2.9, and is exemplified by and preferably selected from among the aforementioned hydrophilic groups.

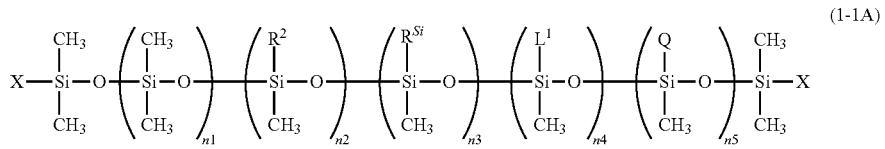

(1-1A)

(In the formula,
$R^2$, $R^{Si}$, $L^1$, and Q are each independently synonymous with those described above; X is a group selected from among the groups comprising a methyl group, $R^2$, $R^{Si}$, $L^1$, and Q; (n1+n2+n3+n4+n5) is a number in a range from 1 to 200; n1 is a number in a range from 0 to 100; n2 is a number in a range from 0 to 100; n3 is a number in a range from 0 to 20; n4 is a number in a range from 0 to 20; and n5 is a number in a range from 0 to 20. However, when n2=0, at least one R is $R^2$, and when n5=0, at least one X is Q.

In formula (1-1A), (n1+n2+n3+n4+n5) is a number in a range from 1 to 200. When (n1+n2+n3+n4+n5) is 1, the diglycerin derivative-modified silicone of the present invention is a diglycerin derivative-modified trisiloxane. From the standpoints of emulsification performance when used as an emulsifier for a water-in-oil emulsion or dispersion performance when used as a powder-in-oil dispersing agent, (n1+n2+n3+n4+n5) is more preferably a number in a range from 1 to 120, and is particularly preferably in a range from 20 to 90. Similarly, n1 is preferably a number in a range from 0 to 100, more preferably in a range from 1 to 70, and still more preferably in a range from 10 to 60. n2 is preferably a number in a range from 1 to 100, more preferably in a range from 1 to 50, and even more preferably in a range from 5 to 30. n3 is preferably a number in a range from 0 to 20, and more preferably in a range from 0 to 10. n4 is preferably a number in a range from 0 to 20, and more preferably in a range from 1 to 10.

When $R^2$ is the long chain alkyl group, from the standpoints of surface activity and compatibility with oil agents other than silicone, it is preferable that n2>1, and is particularly preferable that n2 is within the range of 5 to 30.>

Furthermore, the diglycerinderivative-modified silicone can be a mixture of one or two or more types of a diglycerinderivative-modified silicone expressed by the general formula (1). More specifically, the diglycerin derivative-modified silicone can be a mixture of at least two types of diglycerin derivative-modified silicones, with different types of modified groups, modification rate, and degree of polymerization of the siloxane main chain.

As the diglycerin derivative-modified silicone, a diglycerin derivative-modified silicone represented by the following structural formula (1-1-1) is preferable:

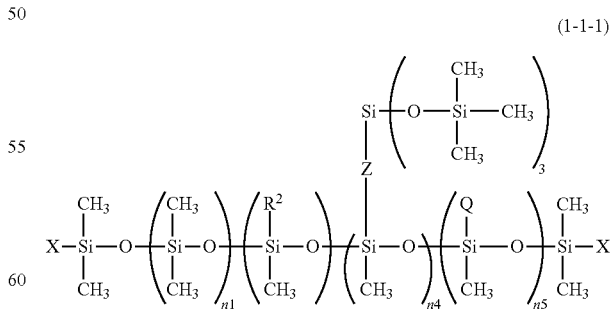

(1-1-1)

(In the formula,
$R^2$, Q, X, Z, n1, n2, n4, and n5 are synonymous with those described above), or the following structural formula (1-1-2):

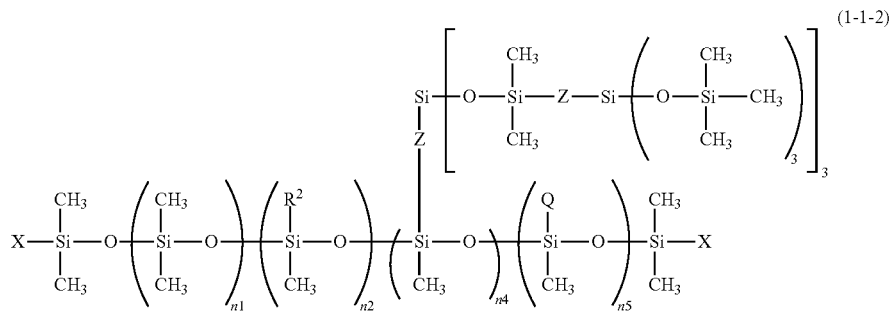

(1-1-2)

(In the formula,
R², Q, X, Z, n1, n2, n4, and n5 are synonymous with those described above).

When consideration is given to an application such as an emulsifier for a water-in-oil emulsion or a powder-in-oil dispersing agent, modification rate of the organopolysiloxane due to the diglycerin derivative-containing organic group is preferably in a range from 0.001 to 15 mol %, more preferably in a range from 0.01 to 10 mol %, and yet more preferably in a range from 0.1 to 5 mol % of all functional groups bonded to polysiloxane, which is the main chain. Furthermore, in the glycerin derivative-modified silicone represented by structural formula (1-1), the modification rate (mol %) resulting from the glycerin derivative group-containing organic group is expressed by the following formula:

Modification rate(mol %)=(number of diglycerin derivative group-containing organic groups bonded to silicon atoms per molecule)/(6+2×(n1+n2+n3+n4))×100

For example, in the case of a diglycerin derivative-modified silicone comprising trisiloxane having one diglycerin derivative group-containing organic group, of the 8 silicon atom bonded functional groups, one is modified by the diglycerin derivative group-containing organic group, so the modification rate by the diglycerin derivative group-containing organic group is 12.5 mol %.

(Synthesis Reaction for a Diglycerin Derivative-Modified Silicone or a Composition Containing the Same)

The diglycerin derivative-modified silicone can be obtained by, for example, reacting (a1) a glycerin derivative having one reactive unsaturated group per molecule, (b1) organopolysiloxane having silicon atom bonded hydrogen atoms, and (c1) a long chain hydrocarbon compound having one reactive unsaturated group per molecule, and if necessary, (d1) a siloxane dendron compound having one reactive unsaturated group per molecule, and/or (e1) a chain organopolysiloxane compound having one reactive unsaturated group per molecule in the presence of a hydrosilylation reaction catalyst. The reactive unsaturated group preferably is an unsaturated functional group having a carbon-carbon double bond, and is exemplified by an alkenyl group or unsaturated carboxylic ester group. In this case, the —R¹ group can be considered to be contained in component (b1); the —R² is introduced by using component (c1), and the -L¹ is introduced by using component (d1).

Furthermore, at this time, by using an excessive amount of component (a1) for the silicon-bonded hydrogen atoms in component (b1), it is possible to obtain a composition comprising a glycerin derivative-modified silicone and component (a1).

More specifically, the diglycerin derivative-modified silicone can be obtained as below, for example.

The glycerin derivative-modified silicone can be obtained by addition reacting with organopolysiloxane having a silicon-hydrogen bond, an unsaturated long chain hydrocarbon compound having a carbon-carbon double bond at one terminal of the molecular chain, and an unsaturated ether compound of a diglycerin derivative having a carbon-carbon double bond in the molecule. Furthermore, a siloxane dendron compound having a carbon-carbon double bond at one terminal of the molecular chain, and/or a chain organopolysiloxane having a carbon-carbon double bond at one terminal of the molecular chain can be further addition reacted. In addition, it is arbitrarily possible to further react the unsaturated short chain hydrocarbon compounds (halogen atom-substituted or unsubstituted) with 2 to 8 carbons, having a carbon-carbon double bond at one terminal of the molecular chain.

In the above case, the glycerin derivative-modified silicone can be obtained as a product of the hydrosilylation reaction between the unsaturated long chain hydrocarbon compound and the glycerin derivative unsaturated ether compound, and arbitrarily the siloxane dendron compound, and/or a chain organopolysiloxane having a carbon-carbon double bond at one terminal of the molecular chain, and/or the unsaturated short chain hydrocarbon compound and a SiH group containing siloxane. As a result, it is possible to introduce into the polysiloxane chain of the diglycerin derivative-modified silicone, a long chain hydrocarbon group, a glycerin derivative group-containing organic group, and arbitrarily a silylalkyl group having a siloxane dendron structure, and/or a chain organopolysiloxane group, and/or a short chain hydrocarbon group. This reaction can be performed as a batch or can take the form of successive reactions. However, successive reactions are preferable from the perspectives of safety and quality control.

For example, the glycerin derivative-modified silicone can be obtained by reacting at least the (b2) organohydrogensiloxane expressed by the following general formula (1'), (a2) a diglycerin derivative having one reactive junsaturated group per molecule, and (c2) a long chain hydrocarbon compound having one reactive unsaturated group per molecule in the presence of a hydrosilylation reaction catalyst.

  (1')

(In the formula,
$R^1$, "a," "b," "c," "d," and "e" are synonymous with those described above) It is preferable to further react (d) a siloxane dendron compound having one reactive unsaturated group per molecule, and/or (e) a chain organopolysiloxane having one reactive unsaturated group per molecule.

The diglycerin derivative-modified silicone can be preferably produced as follows. In the state where (a1) a diglycerin derivative having one reactive unsaturated group per molecule, (c1) a long chain hydrocarbon compound having one reactive unsaturated group per molecule, and arbitrarily (d) a siloxane dendron compound having one reactive unsaturated group per molecule, and/or (e) a chain organopolysiloxane having one reactive unsaturated group per molecule coexist; either the component (a2), the component (c2), and/or the component (d), and/or the component (e), and (b2) an organohydrogensiloxane expressed by the general formula (1') are reacted together; or the organohydrogensiloxane (b2), and arbitrarily the component (d), and/or the component (e) are successively addition reacted, then the component (c2) is addition reacted, and the component (a2) is further addition reacted; and the like.

As (b2) the organohydrogensiloxane used in the synthesis of the diglycerin derivative-modified silicone, an organohydrogensiloxane represented by, for example, the following structural formula (1-1)' is preferable.

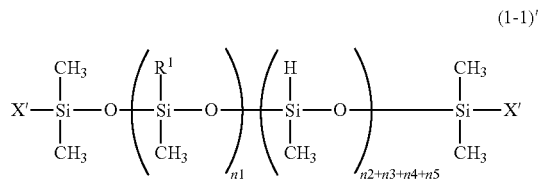  (1-1)'

(In the formula,
$R^1$ are each independently synonymous with that described above;
X' is a group selected from $R^1$ or a hydrogen atom; and n1, n2, n3, n4 and n5 are synonymous with those described above; however, when n2+n3+n4+n5=0, both X' are hydrogen atoms)

The diglycerin derivative-modified silicone is preferably synthesized by subjecting to a hydrosilylation reaction (a) a diglycerin derivative having a carbon-carbon double bond at a terminal of a molecular chain, (c) a long chain hydrocarbon compound having one reactive unsaturated group per molecule, and (b) organohydrogenpolysiloxane; and the organohydrogensiloxane (component (b)) is preferably an organohydrogensiloxane obtained by successively addition reacting the component (d1) and/or the component (e1). In this case, the organohydrogensiloxane immediately prior to reaction with component (a) (after successive reactions with other components) is preferably represented by the following structural formula (1-1A').

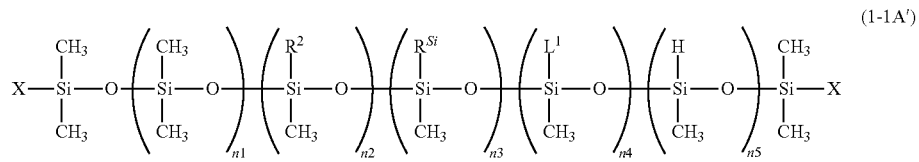  (1-1A')

(In the formula,
$R^2$ and $L^1$ are each independently synonymous with those described above;
X is selected from the groups comprising a methyl group, $R^2$, $L^1$, and a hydrogen atom (H); (n1+n2-1-n3+n4+n5) is a number in a range from 1 to 200; n1 is a number in a range from 0 to 100; n2 is a number in a range from 0 to 100; n3 is a number in a range from 0 to 20; n4 is a number in a range from 0 to 20; and n5 is a number in a range from 0 to 20. However, when n2=0, at least one X is $R^2$; and when n5=0, at least one X is H)

A glycerin derivative having one reactive unsaturated group per molecule, which is used in the synthesis of the glycerin derivative-modified silicone, is preferably (a) a glycerin derivative having a carbon-carbon double bond at the terminal of molecular chain. This is a diglycerin derivative having an allyl diglycerol, allyl diglycidyl ether, diglycerin monoallyl ether, or similar reactive functional group having an alkenyl group or the like at the molecular terminal, and can be synthesized according to a known method.

With the diglycerin derivative-modified silicone according to the present invention, from the perspective of use as a surfactant or dispersing agent that can produce a stable composition having an oil agent as the continuous phase (a water-in-oil emulsion composition or a powder-in-oil dispersion), such as an emulsifier for a water-in-oil emulsion, and from the perspective of use in a cosmetic composition, component (a) is specifically diglycerin monoallyl ether or diglyceryl eugenol.

Preferable examples of (c) the long chain hydrocarbon compound having one reactive unsaturated group in the molecule include monounsaturated hydrocarbons having from 9 to 30 carbons, and more preferably 1-alkenes. Examples of the 1-alkene include 1-nonene, 1-decene, 1-undecene, 1-dodecene, 1-tridecene, 1-tetradecene, 1-hexadecene, 1-octadecene and the like.

(d) The siloxane dendron compound that has one reactive unsaturated group per molecule used in the synthesis of a diglycerin derivative-modified silicone of the present invention, is preferably a compound having a siloxane dendron structure with one carbon-carbon double bond at a molecular terminal, and is expressed by the following general formula (3'):

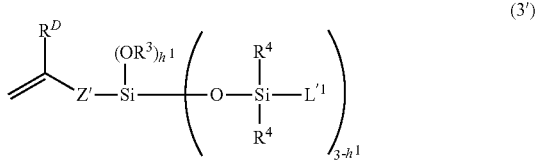

(In the formula,
$R^3$ and $R^4$ are synonymous with those described above, $R^D$ is a hydrogen atom or a methyl group;
Z' is a divalent organic group;
$h^1$ is a number in a range from 0 to 3;
$L'^1$ is the $R^4$ moiety or, when j=1, a silylalkyl group expressed by the following general formula (3"):

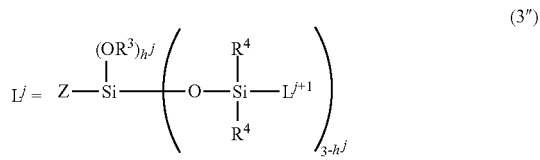

(In the formula, $R^3$ and $R^4$ are synonymous with those described above;
Z is a divalent organic group;
j indicates the number of generations of the silylalkyl group that is represented by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^4$ moiety when j=k'; and
$h^j$ is a number in a range from 0 to 3).

(e) The chain organopolysiloxane having one reactive unsaturated group per molecule used in the synthesis of a diglycerin derivative-modified silicone of the present invention, is preferably a mono unsaturated chain siloxane compound expressed by the following general formula (2-1):

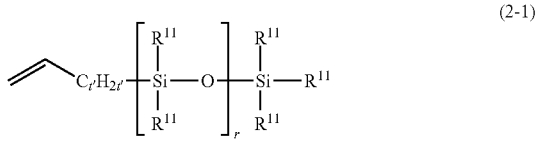

(In the formula, $R^{11}$ is synonymous with the group described above and t' are numbers in a range from 0 to 8 and r is a number in a range from 1 to 500). Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

(f) The unsaturated short chain hydrocarbon compound (halogen atom-substituted or unsubstituted) with 2 to 8 carbons having one reactive unsaturated group per molecule, which can be used in the synthesis of the diglycerin derivative-modified silicone of the present invention, is preferably a monounsaturated hydrocarbon with 2 to 8 carbons, and more preferably a 1-alkene. 1-alkene is preferably exemplified by ethylene, propylene, 1-butene, 1-hexene, 1-octene, and the like.

The hydrosilylation reaction used to synthesize the diglycerin derivative-modified silicone or the composition containing the same can be carried out using a publicly known method in the presence or absence of a solvent. Here, the reaction solvent can be an alcoholic solvent such as ethanol and isopropyl alcohol, an aromatic hydrocarbon-based solvent such as toluene and xylene; an ether-based solvent such as dioxane and THF; an aliphatic hydrocarbon-based solvent such as n-hexane, cyclohexane, n-heptane, cycloheptane and methylcyclohexane; or a chlorinated hydrocarbon-based organic solvent such as carbon tetrachloride.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, and the like; and a platinum complex such as platinum-vinylsiloxane complex, platinum phosphine complex, platinum-phosphite complex, platinum alcoholate catalyst, and the like. If a platinum catalyst is used, the usage quantity of the solvent is approximately 0.0001 to 0.1 wt. %, and preferably 0.0005 to 0.05 wt. % in terms of platinum metal, but is not particularly limited. A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio [amount of substance of carbon-carbon double bonds in glycerin derivative group-containing compound/amount of substance of silicon-bonded hydrogen atoms to be added to the carbon-carbon double bonds of the glycerin derivative group-containing compound in the organohydrogenpolysiloxane] is preferably in a range from 0.8 to 1.5, and more preferably in a range from 1.0 to 1.3. That is, when synthesizing a diglycerin derivative-modified silicone of the present invention, it is more preferable to use a slight excess of diglycerin derivative group-containing compound. Although processing with the ratio above 1.5 is also possible, the proportion of residual raw material increases, so it is not economical. Furthermore, when the ratio is in a range from 0.8 to 1.0, the amount of the silicon-bonded hydrogen atoms consumed by the hydrosilylation reaction falls into the range from 0.8 to 1.0, and silicon-bonded hydrogen atoms remain at the ratio of 0 to 0.2. However, it is possible to cause dehydrogenation reactions with hydroxyl groups contained in the glycerin derivative group and alcoholic hydroxyl groups of the reaction solvent, which can consume the remaining silicon-bonded hydrogen atoms, depending on the reaction conditions.

On the other hand, if the ratio is less than 0.8, there is a risk that unreacted organohydrogenpolysiloxane will remain. When such a diglycerin derivative-modified silicone is used as the raw material for an external use preparation or a cosmetic composition, residual organohydrogenpolysiloxane might react with the other raw materials, and generates hydrogen gas. This might cause such undesirable effects as alteration of the external use preparation or the cosmetic composition at the incorporation destination, fire, container expansion, and the like. In addition, when an attempt is made to consume the remaining silicon-bonded hydrogen atoms by using a dehydrogenation reaction when the ratio is less than 0.8, the proportion of Si—O—C crosslinked bonds increases, which increases the tendency to cause gelation during production. Therefore, to enable the complete and safe consumption of organohydrogenpolysiloxane, it is preferable that the ratio exceeds 0.8, i.e., that 0.8 equivalent or more of the glycerin derivative group-containing compound is reacted.

In addition, when synthesizing the diglycerin derivative-modified silicone according to the present application, it is possible to use the method for reacting, refining and deodorizing with an acidic substance disclosed by the applicants in paragraphs [0110] to [0122] of Patent Document 31 (WO 2011/049248). In particular, the diglycerin derivative-modified silicone of the present invention is mainly used as a cosmetic compositions or external use preparation, and from the perspectives of safety and odor, is most preferably subjected to refining and deodorization with an acidic substance.

From the perspective of deodorization, the diglycerin derivative-modified silicone of the present invention is preferably treated with one or more types of acidic inorganic salt (preferably sodium hydrogensulfate and the like) which is solid at 25° C., which is water-soluble and in which an aqueous solution obtained by dissolving 50 g of the acidic inorganic salt in 1 L of ion exchanged water has a pH of 4 or lower at 25° C. For example, this means (1) carrying out decomposition treatment by adding the aforementioned acidic inorganic salt to a reaction system of a diglycerin derivative-modified polysiloxane composition synthesized using a hydrosilylation reaction, and then stirring and (2) carrying out hydrolysis treatment by adding an acidic inorganic salt and water or an acidic inorganic salt, water and a hydrophilic solvent and then stirring. The treatment process that uses the acidic inorganic salt is preferably carried out in the presence of water and/or a hydrophilic solvent.

After carrying out the aforementioned deodorization treatment, it is preferable to include a stripping step in which low boiling point components (propionaldehyde and the like), which are odor-causing substances, are removed, and it is preferable to carry out the aforementioned treatment using an acidic substance and stripping of odor-causing substances a plurality of times.

Additionally, after the acid treatment process, adding an alkaline buffer (trisodium phosphate, tripotassium phosphate, trisodium citrate, sodium acetate, or the like) at an amount corresponding to 100 ppm to 50,000 ppm in the obtained diglycerin derivative-modified silicone or composition containing the same is preferable from the perspective of reducing odor.

[Applications of Diglycerin Derivative-Modified Silicone]

The diglycerin derivative-modified silicone of the present invention exhibits particularly excellent emulsification performance when used alone, and can therefore finely and stably emulsify/disperse an aqueous phase, powder or the like not only in cases where the oil phase is a silicone oil, ester oil or triglyceride, but also in cases where the oil phase is primarily a non-polar organic oil such as a mineral oil and isododecane, which was difficult with conventional glycerin-modified silicones, and can therefore produce a composition having excellent stability over time or when subjected to heat. In particular, the diglycerin derivative-modified silicone of the present invention can contain a long chain alkyl group, can arbitrarily contain a silylalkyl group having a siloxane dendron structure that is hydrophobic and exhibits high water repellency, and/or a chain polysiloxane group, and can have these and a hydrophilic group within the same molecule. Therefore, the diglycerin derivative-modified silicone of the present invention is extremely useful as a surfactant or dispersing agent that can produce a stable composition having an oil agent as the continuous phase in a wide variety of oil agent systems (a water-in-oil emulsion composition, a polyol-in-oil type emulsion composition, a polar solvent-in-oil type emulsion composition or a powder-in-oil dispersion). The diglycerin derivative-modified silicone of the present invention is particularly preferable as an emulsifier for a water-in-oil emulsion.

In addition, the diglycerin derivative-modified silicone of the present invention can stabilize a wide variety of oil agent-containing emulsion systems in a variety of oil agent-containing W/O emulsion formulations without being aided by an oil gelling agent such as an organic emulsifier, and a clay mineral that has been hydrophobized/oil-swelled by means of a quaternary ammonium salt-based organic cation or the like, and can therefore maximize the synergistic effect in terms of feeling to touch of an oil agent and the diglycerin derivative-modified silicone and provide a W/O emulsion type external use preparation or cosmetic composition having a soft and natural feeling to touch, light smoothness, good spreadability and excellent moisture retention.

In addition, use of the novel diglycerin derivative-modified silicone according to the present invention and/or a composition containing the same as a surfactant is the same as the use of the co-modified organopolysiloxane disclosed by the applicants in paragraphs [0124] to [0147] of the aforementioned Patent Document 31 (WO 2011/049248) as a surfactant and the preparation of a variety of emulsion composition, and the diglycerin derivative-modified silicone according to the present invention is particularly suitable as a surfactant used in a water-in-oil emulsion cosmetic composition.

<Surfactant, Dispersing Agent and Emulsifier for Water-in-Oil Emulsion>

The diglycerin derivative-modified silicone of the present invention can be used as a surfactant or a dispersing agent that can produce a stable composition having an oil agent as the continuous phase (a water-in-oil emulsion composition, a polyol-in-oil type emulsion composition, a polar solvent-in-oil type emulsion composition or a powder-in-oil dispersion). In particular, the emulsifier for a water-in-oil emulsion can be advantageously used not only as an emulsifier for an ordinary water-in-oil emulsion in which an aqueous phase is dispersed in an oil phase, but also as an emulsifier for a polyol-in-oil type emulsion in which a polyol phase is dispersed in an oil phase or as an emulsifier for a polar solvent-in-oil type emulsion in which a polar solvent is dispersed in a non-polar oil phase. Furthermore, the diglycerin derivative-modified silicone of the present invention exhibits excellent performance as a dispersing agent that uniformly disperses a variety of powders in an oil phase, and can therefore also be used as a powder dispersing agent when preparing a water-in-oil emulsion.

A surfactant, dispersing agent and emulsifier for a water-in-oil emulsion that contains the diglycerin derivative-modified silicone of the present invention is suitable for use in a cosmetic composition or external use preparation, and can be preferably blended as a raw material for a variety of cosmetic compositions and external use preparations. In particular, it is preferable to use the diglycerin derivative-modified silicone at a quantity of approximately 0.1 to 40 wt. % relative to the total weight of a cosmetic composition or external use preparation.

Other Uses

The diglycerin derivative-modified silicone according to the present invention can also be used as a tactile sensation improver, a moisturizing agent, a binder, a surface treatment agent, and a skin adhesive. Additionally, the diglycerin derivative-modified silicone according to the present invention can be combined with water for use as a film agent or a viscosity adjusting agent.

Unlike the conventional polyether-modified silicone, the diglycerin derivative-modified silicone of the present invention is hardly susceptible to deterioration due to oxidation by oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT(2, 6-di-t-butyl-p-cresol), vitamin E, or the like, will result in a further increase in stability. In this case, an added amount of the antioxidant that is used is in a range (by weight (mass)) from 10 to 1,000 ppm, and preferably from 50 to 500 ppm, of the diglycerin derivative-modified silicone.

Raw Material for Use in an External Use Preparation or a Cosmetic Composition

The diglycerin derivative-modified silicone of the present invention can be preferably applied as raw material for an external use preparation and a cosmetic composition used on the human body.

A proportion of the diglycerin derivative-modified silicone in the raw material for an external use preparation and a cosmetic composition is preferably from 10 to 100 wt. % (mass %), more preferably from 20 to 100 wt. % (mass %), and even more preferably from 30 to 100 wt. % (mass %), relative to the total weight (mass) of the raw material. This is because the diglycerin derivative-modified silicone according to the present invention can be used as a raw material of an external use preparation or cosmetic composition by diluting the diglycerin derivative-modified silicone in a suitable solvent, such as a silicone oil, an organic oil and an alcohol. A proportion of the raw material compounded in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) based on the total weight (mass) of the external use preparation or the cosmetic composition.

(External Use Preparation and Cosmetic Composition)

The diglycerin derivative-modified silicone of the present invention and/or the composition containing the same of the present invention can be suitably incorporated into an external use preparation or a cosmetic composition, and can form the external use preparations and the cosmetic compositions of the present invention. In particular, the diglycerin derivative-modified silicone of the present invention exhibits particularly excellent emulsification performance when used alone, and can finely and stably emulsify/disperse an aqueous phase, powder or the like not only in cases where the oil phase is a silicone oil, ester oil or triglyceride, but also in cases where the oil phase contains a non-polar organic oil such as a mineral oil and isododecane as a main component, which was difficult with conventional glycerin-modified silicones. As a result, the diglycerin derivative-modified silicone of the present invention can provide a composition having excellent stability over time or when subjected to heat, and can be preferably blended in an external use preparation or cosmetic composition that is in the form of a water-in-oil emulsion.

In addition, the diglycerin derivative-modified silicone of the present invention exhibits far better emulsification performance when used alone than a conventional glycerin-modified silicone, and therefore has the advantage of being able to design a stable formulation or preparation of a cosmetic product without blending a compound having an oxyalkylene structure having an average number of repetitions of an oxyalkylene unit of 2 or higher, and specifically a non-ionic surfactant having a polyoxyalkylene structure. Furthermore, the diglycerin derivative-containing group does not suffer from the problem of oxidative deterioration due to not having a polyoxyethylene (PEG) structure and, unlike a non-ionic surfactant having a polyoxyalkylene structure (for example, a polyether-modified silicone), suppresses oiliness or stickiness in an external use preparation or cosmetic composition that is in the form of a water-in-oil emulsion and can produce a W/O emulsion type external use preparation or cosmetic composition having a soft and natural feeling to touch, light smoothness, good spreadability and excellent moisture retention.

Therefore, the problem of oxidative deterioration of polyoxyethylene (PEG) is substantially ameliorated in an external use preparation or cosmetic composition that contains the diglycerin derivative-modified silicone of the present invention, and it is highly preferable not to blend a compound having an oxyalkylene structure having an average number of repetitions of an oxyalkylene unit of 2 or higher when selecting a completely PEG-FREE formulation as the constitution of an end consumer product having an excellent feeling to touch, such as a cosmetic product. In addition, it is difficult to achieve this objective when using a conventional glycerin-modified silicone rather than the diglycerin derivative-modified silicone of the present invention.

The external use preparation is a product to be applied to human skin, nails, hair, and the like and, for example, medicament active ingredients can be compounded therein and used in the treatment of various disorders. The cosmetic composition is also a product to be applied to human skin, nails, hair, and the like, and is used for beauty purposes. The external use preparation or cosmetic composition is not limited, but is preferably an anti-perspirant, a skin cleansing agent, a skin conditioner, a skin cosmetic composition product, a make-up composition product, an oil-based cosmetic composition product, a skin care cosmetic composition product, a hair cleansing agent, an external use preparation for hair or a hair cosmetic composition product.

The anti-perspirant, skin cleansing agent, skin conditioner or skin cosmetic composition product according to the present invention contains an emulsifier for a water-in-oil emulsion or powder dispersing agent that contains the diglycerin derivative-modified silicone of the present invention, and the form thereof is not particularly limited, but may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Similarly, the hair cleansing agent, hair external use preparation or the hair cosmetic composition product according to the present invention contains the diglycerin derivative-modified silicone of the present invention and can be used in various forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

In addition, the type, form and container of the cosmetic composition or external use preparation composition according to the present invention are the same as those disclosed by the applicants in paragraphs [0230] to [0233] and so on of the aforementioned Patent Document 21 (WO 2011/049248).

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

(E) Powder or Coloring Agent

A powder or coloring agent (E), which is used in the cosmetic composition or external use preparation according to the present invention, is one that is commonly used as a component of a cosmetic composition, and includes white or colored pigments and extender pigments. The white and colored pigments are used to impart color and the like to the cosmetic composition, and the extender pigments are used to improve the feeling to touch and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range from 1 nm to 100 μm. When compounding the powder and/or coloring agent as a pigment, preferably one or two or more selected from an inorganic pigment powder, an organic pigment powder, and a resin powder having an average diameter in a range from 1 nm to 20 μm is compounded.

Examples of the powder include inorganic powders, organic powders, surfactant metal salt powders (metallic soaps), colored pigments, pearl pigments, metal powder pigments, and the like. In addition, compound products of the powders can also be used. Furthermore, it is possible to subject the surface of these to water-repellent treatment.

These specific examples are the same as the powders and coloring agents disclosed by the applicants in paragraphs [0150] to [0152] of the aforementioned Patent Document 31 (WO 2011/049248).

Of the exemplified powders, a particular explanation will be given of a silicone elastomer powder. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group and the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using an emulsifier for a water-in-oil emulsion or powder dispersing agent that contains the diglycerin derivative-modified silicone, it is possible to impart a moist feeling to touch without reducing the suede-like feeling to touch of a silicone elastomer powder. Furthermore, when blending an emulsifier for a water-in-oil emulsion that contains the diglycerin derivative-modified silicone in addition to a silicone elastomer powder in a cosmetic composition, it is possible to improve the dispersion stability of the powder in the overall cosmetic composition and obtain a cosmetic composition that is stable over time.

The silicone elastomer powder can be in various forms such as spherical, flat, amorphous, and the like. The silicone elastomer powder may be in the form of an oil dispersion. With the cosmetic composition of the present invention, a silicone elastomer powder having a particle shape, having a primary particle size in a range of 0.1 to 50 μm observed using an electron microscope and/or the average primary particle size in a range of 0.1 to 50 μm measured by laser diffraction/scattering method, and having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the aforementioned Patent Document 31 (WO 2011/049248), and may be a silicone elastomer powder that has been subjected to a variety of water-repellent treatments, as disclosed in paragraphs [0150] to [0152].

(C) Oil Agent

The oil agent used in the cosmetic composition or external use preparation according to the present invention is preferably one or more oil agents selected from among silicone oils, non-polar organic compounds and lowly polar to highly polar organic compounds that are liquid at 5 to 100° C. (C), and the non-polar organic compound and lowly polar to highly polar organic compound are preferably a hydrocarbon oil, fatty acid ester oil or liquid fatty acid triglyceride. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents. Because an emulsifier for a water-in-oil emulsion or powder dispersing agent that contains the diglycerin derivative-modified silicone exhibits excellent compatibility with, and dispersibility in, these non silicone based oil agents, it is possible to stably blend a hydrocarbon oil or fatty acid ester oil in a cosmetic composition and also possible to utilize the moisture retention characteristics of these non silicone based oil agents. Therefore, an emulsifier for a water-in-oil emulsion or powder dispersing agent that contains the diglycerin derivative-modified silicone can improve the compounding stability in a cosmetic composition of these non silicone based oil agents.

In addition, by using a hydrocarbon oil and/or fatty acid ester oil in combination with a silicone oil, it is possible to retain moisture in the skin in addition to the refreshing feeling to touch inherent in silicone oils and impart a cosmetic composition with a moisturizing feel (also known as a "luxurious feeling to touch") that moisturizes skin and hair and a smooth feeling to touch, and this also has the advantage of not impairing the stability over time of a cosmetic composition. Furthermore, with a cosmetic composition comprising the hydrocarbon oil and/or fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone based oil agent (e.g. a hydrocarbon oil, a fatty acid ester oil, or the like), the cosmetic composition comprising a non silicone based oil agent along with a silicone oil is advantageous in that a smoother, more luxurious feeling to touch is imparted.

These oil agents are the same as those disclosed by the applicants in paragraphs [0130] to [0135] and [0206] and so on in the aforementioned Patent Document 31 (WO 2011/049248). Examples of the fluorine-based oil include perfluoropolyether, perfluorodecalin, perfluorooctane, and the like.

It is possible to further blend water (B) in the cosmetic composition or external use preparation of the present invention, and the cosmetic composition or external use preparation of the present invention may be in the form of a water-in-oil type emulsion. In this case, the cosmetic composition or the external use preparation of the present invention displays superior emulsion stability and sensation during use. The preparation of a hydrous cosmetic composition or emulsion cosmetic composition is the same as that disclosed by the applicants in paragraphs [0128] to [0146] and so on in the aforementioned Patent Document 31 (WO 2011/049248).

It is possible to further blend another surfactant (F) in the cosmetic composition or external use preparation of the present invention. These surfactants are cleansing components for skin or hair or components that function as emulsifiers for oil agents, and can be selected as appropriate according to the type and function of the cosmetic composition. More specifically, other surfactants can be selected from among the group comprising anionic surfactants, cationic surfactants, non-ionic surfactants, amphoteric surfactants and semipolar surfactants, but use in combination with a silicone-based non-ionic surfactant is particularly preferred.

These surfactants are the same as those disclosed by the applicants in paragraphs [0162], [0163] and [0195] to [0201] and so on in the aforementioned Patent Document 31 (WO 2011/049248). The emulsifier for a water-in-oil emulsion that contains the diglycerin derivative-modified silicone used in the present invention has a hydrophilic moiety and a hydrophobic moiety in the molecule, and therefore functions as a powder-in-oil dispersing agent. Therefore, when combined with a silicone-based non-ionic surfactant, the diglycerin derivative-modified silicone functions as an aid to enhance the stability of the non-ionic surfactant, and may improve the overall stability of the formulation. In particular, the diglycerin derivative-modified silicone can be advantageously used in combination with a polyglycerin-modified silicone that is at least "tri-", a glycerin-modified silicone, a sugar-modified silicone and a sugar alcohol-modified silicone. Moreover, as necessary, a silicone-based nonionic surfactant in which an alkyl branch, a straight chain silicone branch, a siloxane dendrimer branch or the like is provided along with the hydrophilic group can be advantageously used. Note that, while it is possible to combine use with a polyoxyalkylene-modified silicone, or an organopolyoxyalkylene group-containing surfactant, from the perspective of increasing environmental compatibility and changing the entire formulation of the cosmetic composition or the external use preparation to a PEG-FREE formulation, a non-polyether structure surfactant is preferably selected.

Depending on the intended use thereof, the cosmetic composition or external use preparation of the present invention can contain one or two or more polyhydric alcohols and/or lower monohydric alcohols as a component (G). These alcohols are the same as those disclosed by the applicants in paragraphs [0159] and [0160] and so on in the aforementioned Patent Document 31 (WO 2011/049248). However, from the perspective of increasing environmental compatibility and changing the entire formulation of the cosmetic composition or the external use preparation to a PEG-FREE formulation, a non-polyether structure polyhydric alcohol and/or lower monohydric alcohol is preferably selected.

Depending on the purpose thereof, the cosmetic composition or the external use preparation of the present invention can include one or two or more inorganic salts and/or organic salts as a component (H). These salts are the same as those disclosed by the applicants in paragraph [0161] and so on in the aforementioned Patent Document 31 (WO 2011/049248).

Depending on the purpose thereof, the cosmetic composition or the external use preparation of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyimide-modified silicone, an alkyl-modified silicone wax, and an alkyl-modified silicone resin wax as a component (I). These silicone components are the same as those disclosed by the applicants in paragraphs [0161] to [0193] and so on in the aforementioned Patent Document 31 (WO 2011/049248).

Depending on the intended use thereof, the cosmetic composition or external use preparation of the present invention can include the following components as component (J): (J-1) silicone polyether elastomer gel that display increased compatibility with various organic components and stable thickening effects due to the introduction of polyoxypropylene groups (commercially available products include Dow Corning EL-8050 ID SILICONE ORGANIC ELASTOMER BLEND, Dow Corning EL-8051 IN SILICONE ORGANIC ELASTOMER BLEND, and Dow Corning EL-7040 HYDRO ELASTOMER BLEND) described in WO2007/109240 and WO2009/006091; and (J-2) the pituitous silicone fluids described in WO2011/028765 and WO2011/028770. Furthermore, the liquid and slightly cross-linkable organopolysiloxane filed in Japan (as patent application 2010-289722) by the present applicant, and for which priority rights are claimed based on the application can be used in the present invention.

Depending on the intended use thereof, the cosmetic composition or external use preparation of the present invention can contain one or two or more water-soluble polymers as a component (K). These water-soluble polymers are the same as those disclosed by the applicants in paragraphs [0201] and so on in the aforementioned Patent Document 31 (WO 2011/049248). However, from the perspective of increasing environmental compatibility and changing the entire formulation of the cosmetic composition or the external use preparation to a PEG-FREE formulation, a non-polyether structure water-soluble polymer is preferably selected.

Depending on the intended use thereof, the cosmetic composition or external use preparation of the present invention can contain one or two or more ultraviolet light blocking components as a component (N). These ultraviolet light blocking components are the same as the organic and inorganic ultraviolet light blocking components disclosed by the applicants in paragraphs [0202] to [0204] and so on in the aforementioned Patent Document 31 (WO 2011/049248). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris [4-(2-ethylhexyloxycarbonyl)anilino]1,3,5-triazine, and 2,4-bis-6-(4-methoxyphenyl)-1,3,5-triazine. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with a powder dispersing agent and an emulsifier for a water-in-oil emulsion that contains the diglycerin derivative-modified silicone in the cosmetic composition or the external use preparation of the present invention, it is possible to stably disperse the ultraviolet light blocking component in the cosmetic composition while improving the feeling to touch and storage stability of the overall cosmetic composition, and it is therefore possible to impart the cosmetic composition with excellent ultraviolet radiation blocking properties.

Various components other than the components described above can be used in the cosmetic composition or external use preparation of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These optional components for cosmetic product are the same as those disclosed by the applicants in paragraphs [0207], [0208] and [0220] to [0228] and so on in the aforementioned Patent Document 31 (WO 2011/049248).

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent. These anti-perspiration components and deodorant components are the same as those disclosed by the applicants in paragraphs [0209] to [0219] and so on in the aforementioned Patent Document 31 (WO 2011/049248). Similarly, in cases where the external use preparation or the cosmetic composition according to the present invention is an anti-perspirant composition, the preparation and method of use of the various anti-perspirant compositions are the same as those disclosed by the applicants in paragraphs [0234] to [0275] and so on of the aforementioned Patent Document 31 (WO 2011/049248).

INDUSTRIAL APPLICABILITY

An emulsifier for a water-in-oil emulsion or powder dispersing agent that contains the diglycerin derivative-modified silicone of the present invention can be advantageously used as a raw material for an external use preparation or cosmetic composition. Furthermore, because of these excellent characteristics, the diglycerin derivative-modified silicone of the present invention is line with the global trend of improving the constitution of an end consumer product such as a cosmetic product to a completely PEG-FREE formulation, and is a key material for providing a water-in-oil emulsion external use preparation or cosmetic composition which exhibits excellent stability, usability and feeling to touch despite not containing a compound having a polyoxyethylene moiety.

EXAMPLES

Hereinafter, the present invention is described in detail with reference to examples. It should be understood that the present invention is not restricted to the examples. In the following compositional formulae, "Me" represents a methyl (—CH$_3$) group, "M" represents a Me$_3$SiO group (or an Me$_3$Si group), "D" represents an Me$_2$SiO group, "D$^H$" represents an MeHSiO group, and "M$^R$" and "D$^R$" respectively represent units in which a methyl group in "M" or "D" is modified by any substituent. Additionally, in the production examples, "IPA" represents isopropyl alcohol.

Production Example 1 for Practical Examples

Synthesis of Diglycerin Derivative-Modified Silicone No. 1

Step 1: 564.0 g of a methylhydrogenpolysiloxane expressed by the average composition formula MD$_{52}$D$^H$$_8$M, and 42.1 g of a vinyl tris(trimethylsiloxy)silane expressed by the average composition formula CH$_2$=CH—Si(OSiMe$_3$)$_3$ were placed in a reaction vessel. Then, 1.11 g of a hexamethyldisiloxane solution of a platinum-1,3-divinyl-1,1,3,3-tetramethyldisiloxane complex (Pt concentration: 0.4 wt. %) was added at 25° C. while agitating under a nitrogen stream. The reaction liquid was heated to 65 to 75° C. and allowed to react for 4 hours. Then, 2 g of the reaction liquid was sampled and it was confirmed that the reaction rate was not in error through an alkali decomposition gas generation method.

Step 2: 51.1 g of hexadecene (a olefin purity=91.7%) was added to the reaction liquid (first adding) and the heat generated thereby caused the temperature to rise from 52° C. to 65° C. After the temperature rise caused by generated heat leveled off, 76.8 g of the hexadecene (second adding) was added and the heat generated again thereby caused the temperature to rise from 51° C. to 67° C. 2 g of the reaction liquid was sampled and it was confirmed by an alkali decomposition gas generation method that the target reaction rate had been achieved.

This Step 2 required about 1 hour.

Step 3: 86.4 g of a diglycerin monoallyl ether, 0.08 g of natural vitamin E, and 480 g of IPA were added to the reaction liquid. Then, 1.78 g of the platinum catalyst solution described above was added. A reaction was allowed to occur for 4 hours at 45 to 65° C., and it was confirmed that the reaction was complete through the method described above.

Step 5: 24 g of a 0.16% phosphoric acid solution and 12 g of purified water were added to the contents of the reaction vessel, and acid treatment was carried out for 2 hours under IPA reflux at 80° C. under stirring and under a nitrogen stream. The reaction liquid was then neutralized by adding 0.67 g of 2.5% aqueous ammonia, the IPA was distilled off under reduced pressure at 70 to 80° C., and stripping was then carried out for 3 hours at a temperature of 95 to 105° C. and a pressure of 10 Torr for 3 hours so as to distill off water and low-boiling components. Then, filtration was carried out so as to obtain 746 g of a composition containing a diglycerin derivative-modified silicone represented by the average composition formulae $MD_{52}D^{R*11}{}_{4.5}D^{R*31}{}_{1}D^{R*22}{}_{2.5}M$ as a tan colored opaque homogeneous liquid.

In this formula, $R^{*11}$=—$C_{16}H_{33}$

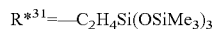

$R^{*22}$ is expressed by —$C_3H_6O$—X, where X is the diglycerin portion.

Production Example 1 for Comparative Examples

Synthesis of Comparative Silicone Compound RE-1

155.9 g of a methylhydrogenpolysiloxane expressed by the average composition formula $MD_{72}D^{H}{}_{12}M$, 13.0 g of a glycerin monoallyl ether represented by the structural formula $CH_2$=CH—$CH_2$—$OCH_2CH(OH)CH_2OH$, 41.1 g of 1-decene, and 63 g of IPA were placed in a reaction vessel, and heated to 45° C. while agitating under a nitrogen stream. 0.055 g of an IPA solution of a platinum-1,3-divinyl-1,1,3,3-tetramethyldisiloxane complex (Pt concentration=4.5 wt. %) was added thereto, and the mixture was reacted for one hour at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 195 g of a tan colored semi-transparent liquid composition comprising a mono-glycerin derivative-modified silicone expressed by the average composition formula: $MD_{72}D^{R*12}{}_{9}D^{R*21}{}_{3}M$ was obtained.

In this formula, $R^{*12}$=—$C_{10}H_{21}$.

Production Example 2 for Comparative Examples

Synthesis of Comparative Silicone Compound RE-2

134.6 g of a methylhydrogenpolysiloxane expressed by the average composition formula $MD_{72}D^{H}{}_{12}M$, 29.9 g of a polyglycerin monoallyl ether, 36.2 g of 1-decene, 200 g of IPA, and 0.25 g of a 2.3% sodium acetate/methanol solution were placed in a reaction vessel, and heated to 55° C. while agitating under a nitrogen stream. 0.16 g of an IPA solution having 5.0 wt. % of chloroplatinic acid was added, and the mixture was reacted for 7 hours at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 180 g of composition comprising a polyglycerin derivative-modified silicone expressed by the average composition formula $MD_{72}D^{R*12}{}_{9}D^{R*24}{}_{3}M$ was obtained. This composition had a gum-like form that was ash-white colored throughout and was not uniform but, rather, partial phase separation (of the gum-like tan colored phase) had occurred.

In this formula, $R^{*12}$=—$C_{10}H_{21}$.

$R^{*24}$ is expressed by —$C_3H_6O$—X, where X is the tetraglycerin portion.

Moreover, the polyglycerin monoallyl ether was synthesized by ring-opening polymerizing 3 mole equivalents of glycidol with 1 mole of a glycerin monoallyl ether, and had a structure in which an average of 4 moles of glycerin were added. Moreover, the glycerin monoallyl ether has two hydroxyl groups that can both react with the glycidol and the polyglycerin portion therefore includes not only a straight chain structure, but also a branched structure.

Production Example 3 for Comparative Examples

Synthesis of Comparative Silicone Compound RE-3

111.6 g of a methylhydrogenpolysiloxane expressed by the average composition formula $MD_{61}D^{H}{}_{15}M$ was placed in a reaction vessel. Then a mixture comprising 30.9 g of a single-terminal vinyl-modified dimethylpolysiloxane represented by the structural formula $CH_2$=$CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature, thereby obtaining a linear siloxane branched-type polysiloxane intermediate.

In addition, 7.0 g of triglycerin monoallyl ether, 50.4 g of dodecene (α olefin purity=95.4%), 100 g of IPA, and 0.40 g of an IPA solution of platinum-1,3-divinyl-1,1,3,3-tetramethyldisiloxane complex (Pt concentration: 0.5 wt. %) were fed into another reaction vessel, and previously synthesized linear siloxane branched-type polysiloxane was added dropwise under solvent reflux, while stirring under a nitrogen stream. After the adding was completed, heating and agitating was continued for 3 hours. Then, 2 g of the reaction liquid was sampled and it was confirmed that the reaction was complete through an alkali decomposition gas generation method.

Next, the reaction liquid was moved to an autoclave and 4.0 g of a sponge nickel catalyst, 2.0 g of water, and 2.0 g of IPA was added. Then, hydrogen gas was introduced and hydrogenation treatment was carried out for 6 hours under the following conditions: 110° C., 0.9 MPa. The reaction mixture was cooled to 60° C. after the treatment and blown with hydrogen gas. Then, purging with nitrogen gas was performed three times. Next, the sponge nickel catalyst was removed via precision filtration. Thus, 204 g of a colorless, transparent filtrate was obtained.

This filtrate was placed in a separate reaction vessel and maintained for one hour at 100° C. and 20 Torr under a nitrogen stream so as to distill off low-boiling components. Thus, 138 g of a substantially colorless, semi-transparent and uniform liquid composition comprising a triglycerin derivative-modified silicone expressed by the average composition formula: $MD_{61}D^{R*13}{}_{12}D^{R*32}{}_{2}D^{R*23}{}_{1}M$ was obtained.

In this formula, $R^{*13}$=—$C_{12}H_{25}$ $R^{*32}$=—$C_2H_4SiMe_2(OSiMe_2)_6OSiMe_3$ $R^{*23}$=—$C_3H_6O$—X, where X is the triglycerin moiety.

Production Example 4 for Comparative Examples

Synthesis of Comparative Silicone Compound RE-4

Step 1: 106.0 g of a methylhydrogenpolysiloxane expressed by the average composition formula $MD_{37}D^{H}{}_{13}M$, and 9.3 g of a vinyl tris(trimethylsiloxy)silane expressed by the average composition formula $CH_2$=CH—$Si(OSiMe_3)_3$ were placed in a reaction vessel. Then, 0.26 g of an IPA solution of a platinum-1,3-divinyl-1,1,3,3-tetramethyldisiloxane complex (Pt concentration: 0.4 wt. %) was added at room temperature while agitating under a nitrogen stream. The mixture was reacted for one hour while heating in an oil bath set to a temperature of 68° C. Then, 2 g of the reaction liquid was sampled and it was confirmed that the reaction rate was not in error through an alkali decomposition gas generation method.

Step 2: 26.6 g of dodecene (a olefin purity=95.4%) was added to the reaction liquid and the heat generated thereby caused the temperature to rise from 35° C. to 61° C. While heating using an oil bath set to 65° C., a reaction was allowed to occur for 1.5 hours, and it was then confirmed that there were no problems in terms of reaction rate in the same way as above.

Step 3: 31.5 g of polyoxyethylene(10)monoallylether, 0.02 g of natural vitamin E, and 60 g of IPA were added to the reaction liquid. Then, 0.25 g of the platinum catalyst solution described above was added. The temperature rose about 4° C. due to the generated heat. A reaction was allowed to occur for 1 hour under the conditions described above, and it was then confirmed that there were no problems in terms of reaction rate in the same way as above.

Step 4: 26.6 g of dodecene was added to the reaction liquid and the heat generated thereby caused the temperature to rise about 8° C. The mixture was reacted for 1.5 hours while heating in an oil bath set to a temperature of 65° C. and, thereafter, it was confirmed that the reaction was complete. Thereafter, the reaction liquid was heated under reduced pressure to remove low-boiling components by distillation.

Step 5: An aqueous solution obtained by dissolving 0.03 g of sodium hydrogensulfate monohydrate in 3 g of purified water was added to the contents of the reaction vessel, and acid treatment was carried out for 30 minutes at 70 to 80° C. under stirring and under a nitrogen stream. After distilling off water and low-boiling components at 70° C. under reduced pressure, the pressure was restored when water droplets in the system had disappeared (first acid treatment). Next, 3 g of water was added and treatment was carried out in the same way for 1 hour, water and other low-boiling components were distilled off, and the pressure was restored when water droplets in the system had disappeared (second acid treatment). After carrying out the same procedure again (third acid treatment), ultrafiltration was carried out so as to obtain 149 g of a composition containing a polyether-modified silicone represented by the average composition formula $MD_{37}D^{R*13}{}_{10}D^{R*31}{}_{1}D^{R*25}{}_{2}M$ as a tan colored clear homogeneous liquid. In this formula, $R^{*13}$=—$C_{12}H_{25}$ $R^{*31}$=—$C_2H_4Si(OSiMe_3)_3$ $R^{*25}$=—$C_3H_6O(C_2H_4O)_{10}H$ The average composition formulae of diglycerin derivative-modified silicone No. 1 according to the present invention, and comparative silicone compound RE1 to comparative silicone compound RE4 according to the comparative examples, which were synthesized according to the methods described above, are as follows.

TABLE 1

| Silicone compound | Average composition formula of modified silicone compound | Properties |
| --- | --- | --- |
| Diglycerin derivative-modified silicone No. 1 | $MD_{52}D^{R*11}{}_{4.5}D^{R*31}{}_{1}D^{R*22}{}_{2.5}M$ (diglycerin-modified) | Tan colored, opaque homogeneous liquid |
| Comparative silicone compound RE-1 | $MD_{72}D^{R*12}{}_{9}D^{R*21}{}_{3}M$ (monoglycerin-modified) | Tan colored, semi-transparent liquid |
| Comparative silicone compound RE-2 | $MD_{72}D^{R*12}{}_{9}D^{R*24}{}_{3}M$ (polyglycerin-modified) | Ash-white gum (partial phase separation) |
| Comparative silicone compound RE-3 | $MD_{61}D^{R*13}{}_{12}D^{R*32}{}_{2}D^{R*23}{}_{1}M$ (triglycerin-modified) | Substantially colorless, semi-transparent, homogeneous liquid |
| Comparative silicone compound RE-4 | $MD_{37}D^{R*13}{}_{10}D^{R*31}{}_{1}D^{R*25}{}_{2}M$ (polyether-modified) | Tan colored, clear, homogeneous liquid |

In the table, the structures and types of the functional groups are as follows.
<Siloxane Branch Group: $R^{*3}$>

$R^{*31}$=—$C_2H_4Si(OSiMe_3)_3$ $R^{*32}$=—$C_2H_4SiMe_2(OSiMe_2)_6OSiMe_3$

<Hydrophilic Group: R*²>

$R^{*21}$=—$C_3H_6OCH_2CH(OH)CH_2OH$ $R^{*22}$=—$C_3H_6O$—X, where X is the diglycerin portion.

$R^{*23}$=—$C_3H_6O$—X, where X is the triglycerine portion.

$R^{*24}$=—$C_3H_6O$—X, where X is the tetraglycerin portion.

$R^{*25}$=—$C_3H_6O(C_2H_4O)_{10}H$

<Other Hydrophobic Organic Group: R*¹>

$R^{*11}$=—$C_{16}H_{33}$ $R^{*12}$=—$C_{10}H_{21}$ $R^{*13}$=—$C_{12}H_{25}$

Practical Examples 1 to 3 and Comparative Examples 1 to 12

Using the silicone compounds obtained in Production Example 1 for practical examples and Production Examples 1 to 4 for comparative examples, water-in-oil emulsion compositions having the formulations shown in Tables 2 and 3 were prepared as described below. These compositions were evaluated in terms of viscosity stability and emulsion particle diameter stability according to the evaluation criteria below. The results are shown in Tables 2 and 3. In the table, "parts" indicates "parts by weight (mass)".

Preparation method for water-in-oil emulsion composition

1. A silicone compound comprising an oil agent and a surfactant was placed in a 200 mL container.
2. The compound was agitated and the surfactant was uniformly dispersed or dissolved in the oil agent (oil phase A).
3. Table salt and ion exchanged water were placed in a separate container. The salt was dissolved by mixing using a spatula. Furthermore, 1,3-butylene glycol was mixed and dissolved therein (aqueous phase B).
4. The saw teeth of the homo-disper were immersed in the oil phase A and, the aqueous phase B was poured into the oil phase A at a constant rate over a period of about 45 seconds, while agitating at 1,000 rpm.
5. The rotational speed of the homo-disper was increased to 3500 rpm, and the contents were homogeneously emulsified by stirring for 2 minutes.
6. Agitation was stopped. Then, the oily component adhered to the inner wall of the container was scraped off using a spatula and mixed with the produced emulsion.
7. The contents were homogeneously emulsified by stirring for 3 minutes with the rotational speed of the homo-disper at 3500 rpm.

Evaluation of Viscosity Stability 28 g of each water-in-oil emulsion composition was measured into a 35 mL glass bottle. The bottles were capped and allowed to sit at rest in a 50° C. constant temperature bath for one month. The viscosity stability of the emulsions before and after sitting was evaluated according to the following standards.

●: Viscosity variation=<±10% and appearance was uniform without change o: ±10%<viscosity variation=<±20% and appearance was uniform Δ: ±20%<viscosity variation=<±30%, or slight decrease in uniformity of the surface of the emulsion.

x: ±30%<viscosity variation, or separation of water drops, aqueous phase, oil phase, or the like. (Cases where the emulsifying itself was not possible are also indicated as "x")

Measurement of emulsified particle size and evaluation of stability Observations and photographs using an optical microscope (at a magnification of 1000 times) were taken on the day after the water-in-oil emulsion compositions were prepared and after allowing the emulsion compositions (after sealing 28 g of the composition in a 35 mL glass bottle, as described above) to stand for 1 month at 50° C., and the weight average particle diameter was calculated using image analysis software. Thereby, stability was evaluated by examining the initial emulsified particle size and the emulsified particle size over time.

Note that notes were made in the tables when particle coalescence was observed.

●: Change in emulsified particle size was small, and signs of coalescence were absent.

o: The emulsified particle size potentially increased slightly but definite coalescence was not observed. Alternatively, the emulsified particle size increased, but the overall particle size was small and the emulsion system was maintained.

Δ: It is thought that partial coalescence of the particles occurred. Definite increase in the maximum emulsified particle size.

x: Many particles were coalesced and emulsion was in the state of breaking down. (Cases where the emulsifying itself was not possible are also indicated as "x")

TABLE 2

Formulations and evaluation results of the water-in-oil emulsion compositions
(Practical Examples 1 to 3 and Comparative Examples 1 to 6)

| Name of raw material | Practical Examples | | | Comparative Examples | | | | | |
|---|---|---|---|---|---|---|---|---|---|
| | 1 | 2 | 3 | 1 | 2 | 3 | 4 | 5 | 6 |
| Diglycerin derivative-modified silicone No. 1 | 2 | 2 | 2 | — | — | — | — | — | — |
| Comparative silicone compound RE-1 | — | — | — | 2 | 2 | 2 | — | — | — |
| Comparative silicone compound RE-2 | — | — | — | — | — | — | 2 | 2 | 2 |

TABLE 2-continued

Formulations and evaluation results of the water-in-oil emulsion compositions
(Practical Examples 1 to 3 and Comparative Examples 1 to 6)

| Name of raw material | Practical Examples | | | Comparative Examples | | | | | |
|---|---|---|---|---|---|---|---|---|---|
| | 1 | 2 | 3 | 1 | 2 | 3 | 4 | 5 | 6 |
| Dimethylpolysiloxane (6 cSt) | 23 | 11.5 | — | 23 | 11.5 | — | 23 | 11.5 | — |
| Mineral oil 50SUS (37.8° C.) | — | 11.5 | 23 | — | 11.5 | 23 | — | 11.5 | 23 |
| Sodium chloride | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 | 6 |
| Viscosity stability of emulsion | ● | ● | ● | X | X | X | ○ | X | X |
| Initial particle diameter (μm) | 3 | 3 | 3 | Separated | | | 5 | 5 (Coalesced) | 4 |
| Particle diameter (μm) after 1 month at 50° C. | 3 | 3 | 3 | Separated | | | 5 (Coalesced) | Separated | |
| Stability of emulsified particles | ● | ● | ● | X | X | X | ○ | X | X |

TABLE 3 water-in-oil emulsion composition formulations and
evaluation results (Comparative Examples 7 to 12)

| Name of raw material | Comparative Examples | | | | | |
|---|---|---|---|---|---|---|
| | 7 | 8 | 9 | 10 | 11 | 12 |
| Comparative silicone compound RE-3 | 2 | 2 | 2 | — | — | — |
| Comparative silicone compound RE-4 | — | — | — | 2 | 2 | 2 |
| Dimethylpolysiloxane (6 cSt) | 23 | 11.5 | — | 23 | 11.5 | — |
| Mineral oil 50SUS (37.8° C.) | — | 11.5 | 23 | — | 11.5 | 23 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Viscosity stability of emulsion | ● | ● | X | ● | ● | ● |
| Initial particle diameter (μm) | 4 | 4 (Coalesced) | 4 | 3 | 3 | 3 |
| Particle diameter (μm) after 1 month at 50° C. | 5 | 5 (Coalesced) | Separated | 3 | 3 | 3 |
| Stability of emulsified particles | ○ | Δ | X | ● | ● | ● |

From the results above, it is clear that only the diglycerin derivative-modified silicone No. 1 (the emulsifier for water-in-oil emulsion that contains the diglycerin derivative-modified silicone of the present invention) exhibited similar emulsification performance to comparative silicone compound RE-4, which is a polyether-modified silicone, of the various glycerin-modified silicones that were tested.

Functionality Evaluation (Tactile Sensation and Sensation During Use)
Next, the water-in-oil emulsion compositions of Practical Example 3, which achieved good results in the stability test, and the water-in-oil emulsion composition of Comparative Example 12 were compared in terms of feeling to touch when used as cosmetic compositions. Specifically:
1. 0.20 g of the water-in-oil emulsion composition was placed on a finger and spread on the back of the hand.
2. In this case, 1) spreadability and smoothness when applying to during application, 2) lack of oiliness during application to after application, 3) lack of film sensation (stickiness when dry) after application, and 4) durability of moisturizing feel were evaluated according to the following standards.

Spreadability and smoothness: Applying to during application
●: Smooth tactile sensation and spread easily without effort
o: Smooth tactile sensation and spread easily
Δ: Initial smoothness was experienced, but spreadability was lacking. Resistance (stickiness and adhesion when dry) with progressive spreading was experienced.
x: Heavy, poor spreadability or noticeable stickiness when initially applied.

Lack of oiliness: During application to after application
●: A pleasant, water-like tactile sensation that lasted until the latter part of application.
Because oiliness is controlled in order to obtain an excellent moisturizing feel, an extremely natural sensation during use with no discomfort in terms of appearance or sensation can be obtained.
o: While fading out from during application to after application, a wet (water-like) tactile sensation remained in trace amounts. Thus, a tactile sensation in which oiliness is balanced was obtained.
Δ: While a wet tactile sensation was experienced during initial application, this sensation disappears quickly and oiliness became predominant.
x: Tactile sensation was oily from initial application and the surface of the skin appeared very oily.

Lack of film sensation: After application
●: Nearly no sensation of stickiness (film sensation) when dry
o: Slight sensation of stickiness (film sensation) when dry
Δ: Stickiness (film sensation) when dry experienced
x: Strong, unpleasant sensation of stickiness at latter part of application Durability of moisturizing feel: 10 minutes after application
●: Luxurious moisturizing feel lasted and there was a natural feeling with no discomfort
o: Moisturizing feel remained, but skin felt slightly drier than immediately after application. Some oiliness was visible.
Δ: No moisturizing feel and oily shine was noticeable.
x: Discomfort and irritation of the skin due to drying was felt

TABLE 4

Functional evaluation results of water-in-oil emulsion compositions (Practical Example 3 and Comparative Example 12)

| Technical classification | Emulsifier | Feeling to touch and feeling of use | | | |
| --- | --- | --- | --- | --- | --- |
| | | Smoothness/ spreadability | Suppression of oiliness | Lack of film sensation | Moisturizing feel durability |
| Practical Example 3 | Diglycerin derivative-modified silicone No. 1 | ○ | ● | ● | ● |
| Comparative Example 12 | Comparative silicone compound RE-4 | ● | Δ | ○~Δ | Δ |

From the results above, it is clear that water-in-oil emulsion composition that contains the aforementioned diglycerin derivative-modified silicone No. 1 (emulsifiers for a water-in-oil emulsion containing the diglycerin derivative-modified silicone of the present invention) was comprehensively superior to a water-in-oil emulsion composition that contains comparative silicone compound RE-4, which is a polyether-modified silicone, in terms of feeling to touch and sensation during use, could sustainably suppress oiliness, which has long been a problem with W/O formulations, while being emulsifiers, and could maintain moisture retention after application despite having the unique characteristic of not causing stickiness.

Therefore, an emulsifier for a water-in-oil emulsion that contains the diglycerin derivative-modified silicone of the present invention exhibits the excellent W/O emulsification performance shown in Table 2 and the excellent effect as a feeling to touch improvement agent or moisturizing agent shown in Table 4, and has therefore been verified as being extremely useful as a raw material for an external use preparation or cosmetic composition. A powder dispersing agent and an emulsifier for a water-in-oil emulsion that contain the diglycerin derivative-modified silicone of the present invention can preferably be used as a raw material for an external use preparation or a cosmetic composition. Because of these excellent characteristics, the diglycerin derivative-modified silicone of the present invention is in line with the global trend of improving the constitution of an end consumer product such as a cosmetic product to a completely PEG-FREE formulation, and can provide a water-in-oil emulsion external use preparation or cosmetic composition which exhibits excellent stability, usability and feeling to touch despite not containing a compound having a polyoxyethylene moiety.

Hereinafter, formulation examples of the cosmetic composition and the external use preparation according to the present invention are described, but it is understood that the cosmetic composition and the external use preparation according to the present invention are not limited to the types and compositions recited in these formulation examples.

Formulations Already Disclosed in Previous Applications

The diglycerin derivative-modified silicone of the present invention can be used for various external use preparations and cosmetic compositions. Specific formulation examples thereof include those obtained by replacing components corresponding to silicone compounds No. 1 to No. 16 in the various external use preparation and cosmetic composition formulations disclosed by the applicants in the practical examples and so on in the aforementioned Patent Document 31 (WO 2011/049248) with the aforementioned diglycerin derivative-modified silicones according to the present invention (for example, diglycerin derivative-modified silicone No. 1), and such examples are encompassed by the scope of the invention of the present application as formulation examples of the cosmetic composition or external use preparation according to the present invention.

In addition, formulations obtained by replacing components corresponding to silicone compounds No. 1 to No. 16 in the various external use preparation and cosmetic composition formulations disclosed by the applicants in the practical examples and so on in the aforementioned Patent Document 31 (WO 2011/049248) with the aforementioned diglycerin derivative-modified silicone according to the present invention (for example, the diglycerin derivative-modified silicone No. 1) and, in cases where compounds containing a polyoxyethylene group or polyoxyethylene moiety are used in the formulation, replacing these compounds with arbitrary non-PEG structure replacement materials or the diglycerin derivative-modified silicone according to the present application are encompassed by the scope of the invention of the present application as formulation examples of the cosmetic composition or external use preparation according to the present invention. For example, in the composition that uses polyether-modified silicone in the formulation examples, a PEG free formulation can be designed and implemented by using the diglycerin derivative-modified silicone of the present invention to replace the materials.

Specifically, the practical examples and so on in the aforementioned Patent Document 31 disclose milky lotions, lip glosses, oil-based foundations, water-in-oil emulsion transparent anti-perspirant compositions and non-aqueous stick-form anti-perspirant compositions as compositions able to be replaced by the diglycerin derivative-modified silicone according to the present invention, and paragraphs [0459] to [0501] in the aforementioned Patent Document 31 also disclose the following formulation examples. Using the diglycerin derivative-modified silicone of the present invention further improves stability with respect to the passage of time and the temperature, when the dosage form is a W/O emulsion. In addition, because the diglycerin derivative-modified silicone of the present invention has excellent compatibility with not only silicone oils, but also a wide range of organic oils, homogeneity and compounding stability is further improved in non-aqueous formulations and powder-containing formulations, and the effect and quality of cosmetic compositions is therefore increased.

Example 1

Emulsion Foundation

Example 2

Liquid Foundation

Example 3

Foundation

Example 4

Water-in-Oil Cream

Example 5

Water-in-Oil Emulsion Composition

Example 6

Water-in-Oil Emulsion Lipstick (Liquid)

Example 7

Liquid Rouge

Example 8

Rouge

Example 9

Sunscreen Emulsion

Example 10

Emulsion

Example 11

UV Blocking Cream

Example 12

UV Blocking Water-in-Oil Emulsion

Example 13

Sunscreen Agent

Example 14

Water-in-Oil Emulsion Sunscreen

Example 15

O/W Cream

Example 16

Eye Shadow

Example 17

Mascara

Example 18

Mascara

Example 19

Solid Powder Eye Shadow

Example 20

Pressed Powder Cosmetic

Example 21

Powder Foundation

Example 22

Pressed Foundation

Example 23

Cream

Example 24

Foundation

Example 25

Water-in-Oil Emulsion-Type Sunscreen

Example 26

Lipstick

Example 27

Rouge

Example 28

Foundation

Example 29

Anti-Perspirant Aerosolized Cosmetic Composition

Example 30

Nonaqueous Pressurized Anti-Perspirant Product

Example 31

Aerosol Type Anti-Perspirant Composition

Example 32

Anti-Perspirant Lotion Composition

Example 33

W/O Emulsion-Type Skin External Use Preparation

Example 34

Nonaqueous Anti-Perspirant Deodorant Stick Composition

Example 35

W/O Solid Anti-Perspirant Stick Composition

Example 36

W/O Emulsion Type Anti-Perspirant Cream Composition

Example 37

Mascara

Example 38

Aftershave Cream

Example 39

Solid Foundation

Example 40

Daytime Use Skin-Lightening Cream

Example 41

Sun Tanning Cream

Example 42

Polyol/O-Type Nonaqueous Emulsion Skin External Use Preparation

Example 43

Polyol/O-Type Nonaqueous Emulsion Skin External Use Preparation

Other Formulations

In addition, for example, it is also possible to design PEG-FREE formulations having the following hydrocarbon system cosmetic composition base materials as the main constituents, by using the diglycerin derivative-modified silicone No. 1 (Practical Example 1) of the present invention.

Formulation Example

Liquid Foundation (W/O)

| (Components) | |
|---|---|
| 1. Isododecane | 20 parts |
| 2. Isohexadecane | 10 parts |
| 3. Isotridecyl isononanoate | 3 parts |
| 4. Glyceryl tricapryl-caprate | 2 parts |
| 5. The diglycerin derivative-modified silicone No. 1 | 2.0 parts |
| 6. Organo-modified clay mineral (Bentone 38V) | 1.5 parts |
| 7. Octyl methoxycinnamate | 5 parts |
| 8. Octylsilane treated titanium oxide | 8.5 parts |

-continued

| (Components) | |
|---|---|
| 9. Octylsilane treated red iron oxide | 0.4 parts |
| 10. Octylsilane treated yellow iron oxide | 1 part |
| 11. Octylsilane treated black iron oxide | 0.1 parts |
| 12. Dimethicone, dimethicone crosspolymer*1 | 2 parts |
| 13. Copolymer of isododecane and (acrylates/polytrimethylsiloxy methacrylate)*2 | 1 part |
| 14. Trimethylsiloxysilicate | 1 part |
| 15. 1,3-butylene glycol | 5 parts |
| 16. Glycerin | 3 parts |
| 17. Sodium chloride | 0.5 part |
| 18. Preservative | q.s. |
| 19. Purified water | Remainder |
| 20. Perfume | q.s. |

Note
*1DC9045, manufactured by Dow Corning

Note
*2FA-4002ID, manufactured by Dow Corning Toray Co., Ltd.

Production Method

Step 1: Components 1, 2, 5, 6, 7, 12, 13, and 14 are agitated and mixed.

Step 2: Components 3, 4, and 8 to 11 are kneaded and mixed using a three-roll mill.

Step 3: While agitating, add the compound of Step 2 to the compound obtained in Step 1 and agitate and mix further.

Step 4: An aqueous phase formed by uniformly dissolving components 15 to 20 is added to the mixture obtained in Step 3, emulsified, and a container is filled with the emulsion. Thus, a product is obtained.

The obtained W/O type liquid foundation has no unpleasant odor, has excellent emulsion stability when used, has excellent moisture resistance and cosmetic durability, has excellent texture, masks wrinkles, has a light feeling to touch, and has excellent adhesion and moisturizing effect durability.

The invention claimed is:

1. A diglycerin derivative-modified silicone that has a halogen atom-substituted or unsubstituted monovalent hydrocarbon group having from 16 to 30 carbons per molecule, that has only a glycerin derivative group, wherein the glycerin derivative group is a diglycerin derivative group-containing organic group expressed by the following general formula (5-1):

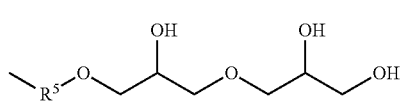

(5-1)

wherein, $R^5$ is a divalent organic group that does not comprise an oxyalkylene structure wherein an average value of the number of repetitions of the oxyalkylene unit is two or more, or the following general formula (5-2):

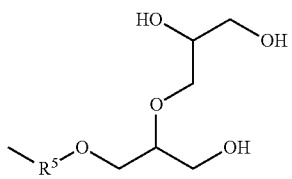
(5-2)

wherein, $R^5$ is as defined above; and that does not have an oxyalkylene structure wherein an average value of the number of repetitions of the oxyalkylene unit is two or more and that does not have an oxyalkylene derivative group having an oxyalkylene structure wherein an average value of the number of repetitions of the oxyalkylene unit is two or more, or a (poly)glycerin derivative group, excluding the diglycerin derivative group-containing organic group expressed by the general formula (5-1) or the general formula (5-2).

2. The diglycerin derivative-modified silicone according to claim 1 expressed by following general formula (1):

(1)

wherein, $R^1$ is a halogen atom-substituted or unsubstituted monovalent hydrocarbon group having 1 to 8 carbons, alkoxy group, hydrogen atom, or hydroxyl group;

$R^2$ is a halogen atom-substituted or unsubstituted monovalent hydrocarbon group having 16 to 30 carbons;

$R^{Si}$ is a chain organosiloxane group expressed by the following general formula (2-1):

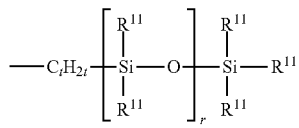
(2-1)

wherein, $R^{11}$ are halogen atom-substituted or unsubstituted monovalent hydrocarbon groups having from 1 to 30 carbons, hydroxyl groups, or hydrogen atoms, and at least one of the $R^{11}$ moieties is the monovalent hydrocarbon group; t is a number in a range of 2 to 10; and r is a number in a range of 1 to 500; or the following general formula (2-2):

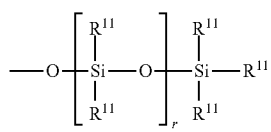
(2-2)

wherein, $R^{11}$ and r are as defined above;

$L^1$ represents a silylalkyl group having a siloxane dendron structure expressed by the following general formula (3) when i=1;

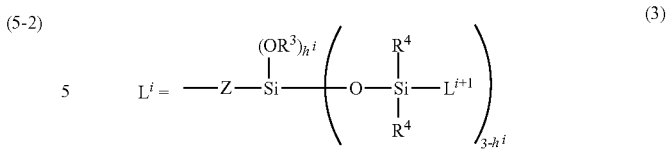
(3)

wherein, $R^3$ represents a halogen atom-substituted or unsubstituted, straight or branched monovalent hydrocarbon group having 1 to 30 carbons; $R^4$ each independently represents a phenyl group or an alkyl group having from 1 to 6 carbons; Z represents a divalent organic group; i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^4$ moiety when i=k; and $h^i$ is a number in a range of 0 to 3;

Q is the diglycerin derivative group-containing organic group expressed by the general formula (5-1) or the general formula (5-2); and a, b, c, d, and e, are values within the ranges $1.0 \leq a \leq 2.5$, $0 < b \leq 1.5$, $0 \leq c+d \leq 1.5$, and $0.001 \leq e \leq 1.5$.

3. The diglycerin derivative-modified silicone according to claim 1, wherein the glycerin derivative group is the diglycerin derivative group-containing organic group expressed by the general formula (5-1) or the general formula (5-2) bonded to silicon atoms via a linking group that is at least divalent, and having one or more glycerin units selected from among the hydrophilic units represented by structural formulae (4-1) to (4-3) below, but which does not comprise an oxyalkylene structure wherein an average value of the number of repetitions of the oxyalkylene unit is two or more in the same functional group;

(4-1)

wherein, W is a hydrogen atom or an alkyl group having from 1 to 20 carbons;

(4-2)

wherein, W is as defined above;

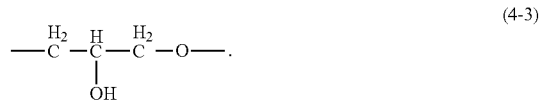
(4-3)

4. The diglycerin derivative-modified silicone according to claim 1, represented by the structural formula (1-1) below:

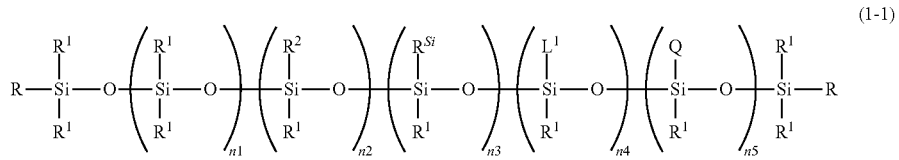

(1-1)

wherein, $R^1$, $R^2$, $R^{Si}$, $L^1$, and Q are as defined above; and R are selected from among $R^1$, $R^2$, $R^{Si}$, $L^1$, and Q; with the proviso that when n2=0, at least one R is $R^2$, and when n5=0, at least one R is Q; (n1+n2+n3+n4+n5) is a number in a range from 1 to 200; n1 is a number in a range from 0 to 100; n2 is a number in a range from 0 to 100; n3 is a number in a range from 0 to 20; n4 is a number in a range from 0 to 20; and n5 is a number in a range from 0 to 20.

5. A composition comprising the diglycerin derivative-modified silicone according to claim 1.

6. A surfactant or dispersing agent comprising the diglycerin derivative-modified silicone according to claim 1.

7. The surfactant or dispersing agent according to claim 6, wherein the surfactant or dispersing agent is used to prepare a composition having an oil agent as a continuous phase.

8. The surfactant according to claim 6, which is an emulsifier for a water-in-oil emulsion.

9. A water-in-oil emulsion composition comprising the diglycerin derivative-modified silicone according to claim 1.

10. A water-in-oil emulsion composition comprising:
(A) the diglycerin derivative-modified silicone according to claim 1,
(B) water, and
(C) at least one oil agent that is liquid at 5 to 100° C. selected from among the group comprising silicone oils, non-polar organic compounds and polar organic compounds.

11. The water-in-oil emulsion composition according to claim 9, which does not comprise a compound having an oxyalkylene structure having an average number of repetitions of an oxyalkylene unit of two or higher.

12. An external use preparation or cosmetic composition comprising the diglycerin derivative-modified silicone according to claim 1.

13. An external use preparation or a cosmetic composition comprising the water-in-oil emulsion composition according to claim 9.

14. The external use preparation or cosmetic composition according to claim 12, which is in the form of a water-in-oil emulsion.

15. The external use preparation or cosmetic composition according to claim 12, which does not comprise a compound having an oxyalkylene structure wherein an average value of the number of repetitions of the oxyalkylene unit is two or more.

* * * * *